(12) United States Patent
Bauer et al.

(10) Patent No.: US 12,039,741 B2
(45) Date of Patent: Jul. 16, 2024

(54) APPARATUS AND METHOD FOR DETERMINING MOTION OF AN ULTRASOUND PROBE INCLUDING A FORWARD-BACKWARD DIRECTEDNESS

(71) Applicant: PIUR IMAGING GMBH, Vienna (AT)

(72) Inventors: Robert Bauer, Unterhaching (DE); Frederik Bender, Vienna (AT)

(73) Assignee: PIUR IMAGING GMBH, Vienna (AT)

( * ) Notice: Subject to any disclaimer, the term of this patent is extended or adjusted under 35 U.S.C. 154(b) by 379 days.

(21) Appl. No.: 17/436,130

(22) PCT Filed: Mar. 6, 2020

(86) PCT No.: PCT/EP2020/056106
§ 371 (c)(1),
(2) Date: Sep. 3, 2021

(87) PCT Pub. No.: WO2020/178445
PCT Pub. Date: Sep. 10, 2020

(65) Prior Publication Data
US 2022/0148199 A1     May 12, 2022

(30) Foreign Application Priority Data

Mar. 6, 2019 (EP) .................................... 19161053

(51) Int. Cl.
*G06T 7/246*     (2017.01)
*A61B 8/00*      (2006.01)
*A61B 8/08*      (2006.01)

(52) U.S. Cl.
CPC ............ *G06T 7/246* (2017.01); *A61B 8/4263* (2013.01); *A61B 8/483* (2013.01); *A61B 8/5292* (2013.01);

(Continued)

(58) Field of Classification Search
None
See application file for complete search history.

(56) References Cited

U.S. PATENT DOCUMENTS

2007/0167821 A1* 7/2007 Lee .......................... A61B 8/12
                                                                  600/463
2010/0010348 A1* 1/2010 Halmann ............. A61B 8/0841
                                                                  600/443

(Continued)

OTHER PUBLICATIONS

Laporte, Catherine, and Tal Arbel. "Learning to estimate out-of-plane motion in ultrasound imagery of real tissue." Medical image analysis 15.2 (2011): 202-213. (Year: 2011).*

(Continued)

*Primary Examiner* — Samah A Beg
(74) *Attorney, Agent, or Firm* — Meunier Carlin & Curfman LLC

(57) ABSTRACT

A method and an apparatus for determining a three-dimensional directedness-determined motion are provided, including a forward-backward directedness, characterizing the motion of a movable ultrasound probe (10) during acquisition of an ultrasound image of a volume portion (2) by the ultrasound probe. The method comprises determining, by a machine-learning module (50), a motion indicator (60) indicating a three-dimensional motion between the ultrasound image frames (22); and determining, by a directedness-determining system (56), a directedness indicator (66) of the three-dimensional motion between the ultrasound image frames (22). The method further comprises determining a directedness-determined motion indicator (96) indicating the three-dimensional directedness-determined motion, including a determined the forward-backward directedness of the motion, between the ultrasound image frames (22) from the motion indicator (60) and the directedness indicator (66).

18 Claims, 9 Drawing Sheets

(52) U.S. Cl.
CPC .............. *G06T 2207/10132* (2013.01); *G06T 2207/20081* (2013.01); *G06T 2207/20084* (2013.01); *G06T 2207/30204* (2013.01)

(56) References Cited

U.S. PATENT DOCUMENTS

| | | | |
|---|---|---|---|
| 2017/0086785 A1* | 3/2017 | Bjaerum | ............... A61B 8/4444 |
| 2017/0116748 A1 | 4/2017 | Scutaru et al. | |
| 2017/0252002 A1 | 9/2017 | Mine et al. | |
| 2018/0235580 A1* | 8/2018 | Park | .................... G01S 15/8979 |
| 2022/0273267 A1* | 9/2022 | Yang | ....................... A61B 8/463 |

OTHER PUBLICATIONS

Prevost, Raphael, et al. "3D freehand ultrasound without external tracking using deep learning." Medical image analysis 48 (2018): 187-202. (Year: 2018).*

International Search Report and Written Opinion mailed May 4, 2020 in PCT/EP2020/056106 (17 pages).

Prevost, Raphael et al., "Deep Learning for Sensorless 3D Freehand Ultrasound Imaging," Sep. 4, 2017, International Conference on Computer Analysis of Images and Patterns, Berlin, Heidelberg, pp. 628-636.

Office Action in connection to Chinese Application No. 2020800185995, dated Feb. 10, 2022.

Search Report in connection to Chinese Application No. 2020800185995, dated Feb. 7, 2022.

Prevost, et al. "3D freehand ultrasound without external tracking using deep learning", Medical Image Analysis. (2018) pp. 197-202.

* cited by examiner

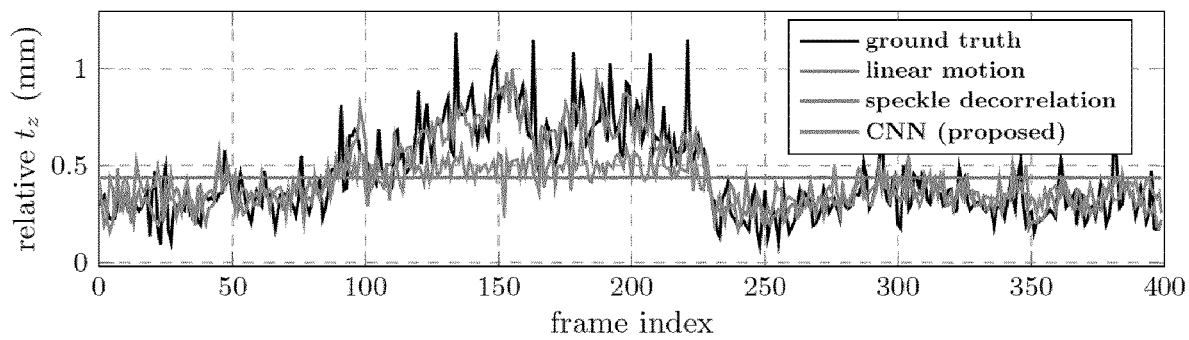
Fig. 7
Fig. 8a
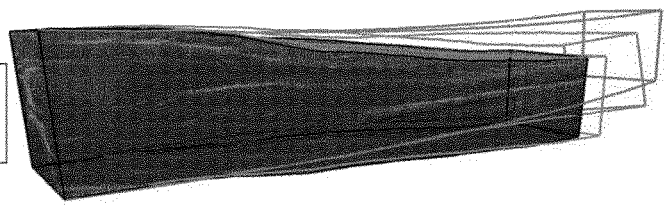
Fig. 8b
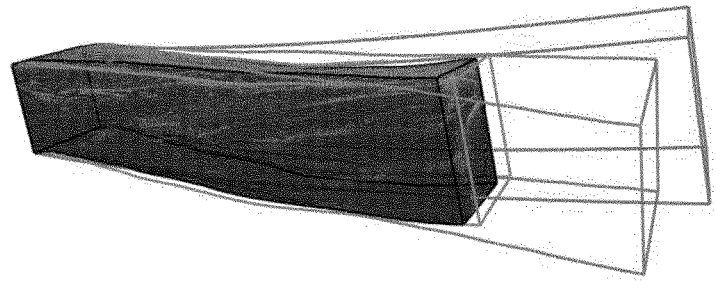
Fig. 8c
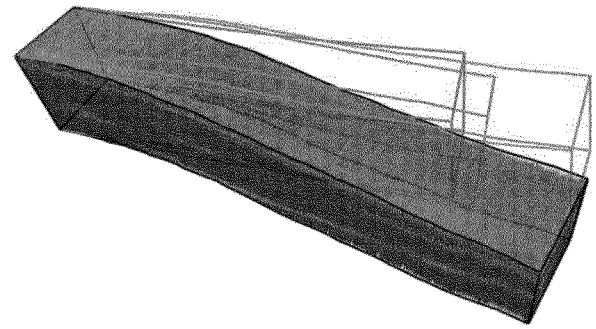

APPARATUS AND METHOD FOR DETERMINING MOTION OF AN ULTRASOUND PROBE INCLUDING A FORWARD-BACKWARD DIRECTEDNESS

CROSS REFERENCE TO RELATED APPLICATIONS

This application is a United States National Phase Patent Application of International Patent Application Number PCT/EP2020/056106, filed on Mar. 6, 2020, which claims benefit of and priority to EP Application No. 19161053.4, filed on Mar. 6, 2019, the contents of which are fully incorporated by reference herein in their entireties.

Aspects of the present application generally relate to a method of determining a three-dimensional directedness-determined motion of a movable ultrasound probe, i.e. including an information regarding the forward-backward directedness of the motion (with respect to the ultrasound probe). The method is, in particular, carried out during acquisition of an ultrasound image of a volume portion by the ultrasound probe. The method comprises, in particular, the determining of a three-dimensional directedness-determined motion indicator indicating the relative three-dimensional directedness-determined motion between ultrasound image frames. Aspects of the present application also relate to a corresponding apparatus for determining a three-dimensional directedness-determined motion of an ultrasound probe.

TECHNICAL BACKGROUND

Ultrasound imaging (ultrasound) is one of the main medical modalities for both diagnostic and interventional applications thanks to its unique properties—affordability, availability, safety and real-time capabilities. For a long time, though, it has not been possible to acquire 3D images in a simple and reliable manner, and this limitation has reduced the range of clinical applications of ultrasound. The workaround was to acquire a series of 2D images by sweeping over the region of interest and combining them into a single volume afterwards.

One such implementation is, for example, described in WO 2015/191871 A1. This implementation requires a positioning system providing probe position information. External sensor-based solutions (typically using optical or electromagnetic tracking) are able to provide a good estimate of the ultrasound probe motion, and have therefore been primarily used. However, these solutions come at the expense of practicality and price.

Thus, research has been conducted for estimating the ultrasound probe motion, i.e., the relative position and orientation of the ultrasound probe from one image to the next, without additional hardware, by estimating the relative position of two images with pure image processing algorithms. It has been found that algorithms like "optical flow" allow estimating the in-plane motion quite reliably. However, estimating the out-of-plane motion (elevational displacement) remains a challenge.

One approach for estimating the out-of-plane motion, described for instance in U.S. Pat. No. 6,012,458, has been to exploit speckle noise patterns that are visible in ultrasound images, and is thus called "speckle decorrelation". "Speckle decorrelation" is based on the assumption that the elevational distance can be estimated by selecting and isolating speckles from the ultrasound images, and by comparing speckles of successive images: The higher the correlation between the speckles, the lower the elevational distance. However, one challenge remains the definition of the speckles and their correspondence across images. For these reasons, the existing "speckle decorrelation" method has been successfully applied only in rather specialized situations, and may not be successful in all real-life scenarios.

The above approaches, and other approaches based on evaluating few consecutive ultrasound images, have in common that the algorithm may need a large amount of training data and/or may have difficulties to distinguish a forward motion from a backward motion (in which the motion vector is multiplied by (−1) relative to the forward motion).

SUMMARY OF THE INVENTION

The present invention intends to overcome at least some of the above problems. The object is solved by the method according to claim 1, and by the apparatus according to claim 17. Further advantages, features, aspects and details of the invention are evident from the dependent claims, the description and the drawings.

Thus, the method according to an aspect of the invention aims at bypassing the previous approaches, such as the speckle decorrelation model, which were based on pre-selected parts or features of ultrasound images. Instead, according to this aspect, the method provides an end-to-end solution with a fully machine learning-based approach, using image data representing entire ultrasound image frames as an input, without selection of any image portions or features. Furthermore, aspects of the invention do not require any assumptions regarding the content of the image, such as the presence of speckles. Therefore, the method works with a broad range of application.

In addition, the method according to an aspect of the invention allows determining a forward-backward directedness, i.e. distinguish a forwardly directed motion from a backwardly directed motion. Here, "forward" and "backward" refers to (arbitrarily assigned) opposite sides of the ultrasound probe along a line perpendicular to the ultrasound image plane. The forward-directed motion is related to a corresponding backward-directed motion by a forward-backward symmetry (e.g., a multiplication of the motion vector by (−1)).

It turns out that while the ultrasound images contain rich information regarding the relative movement of the ultrasound probe, the underlying problem is invariant or agnostic with respect to the forward-backward symmetry. This is the reason for which a machine-learning approach based on evaluating few consecutive ultrasound images may have difficulties to distinguish a forward motion from a backward motion. According to an aspect of the invention, a method is proposed for resolving this ambiguity in a manner that leverages the machine learning-based approach in an efficient manner.

BRIEF DESCRIPTION OF FIGURES

The invention will be better understood by reference to the following description of embodiments of the invention taken in conjunction with the accompanying drawings, wherein:

FIG. 1b shows schematically a compounded three-dimensional ultrasound image obtained by the probe of FIG. 1a;

FIG. 2 shows schematically details of the method for acquiring the three-dimensional image illustrated in FIG. 1a;

FIG. 7 shows predictions of the elevational translation according to comparative examples and according to embodiments of the invention, respectively; and FIG. 8a-8c show 3D visualizations of tracked ultrasound sweeps according to comparative examples and according to embodiments of the invention, respectively;

DETAILED DESCRIPTION

Figure 1A:
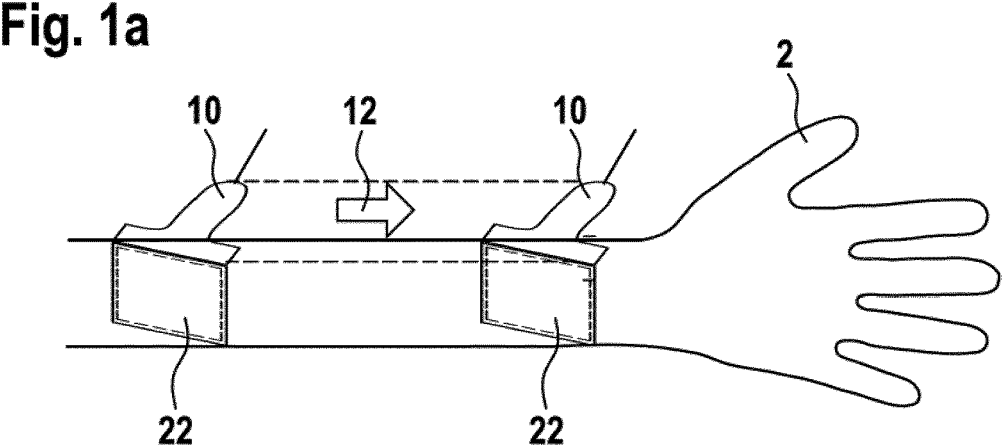
FIG. 1a shows schematically an ultrasound probe used in a method according to an embodiment of the invention.

FIG. 1a shows an ultrasound probe 10 being moved along a volume portion 2. Here, the volume portion 2 is a body portion of a patient. The motion of the probe is indicated by an arrow 12 representing the motion from a starting position (probe 10 shown on the left side of FIG. 1a) to a final position of motion (probe 10 shown on the right side of FIG. 1a). During the motion, the probe 10 collects ultrasound image data representing consecutive ultrasound image frames. Each ultrasound image frame provides an ultrasound image (i.e., graphically representable information of the ultrasound reflectivity properties) in a particular imaging region or image plane 22, i.e., in a two- or three-dimensional subspace of the volume portion 2. The imaging region 22 has a predetermined shape and location relative to the ultrasound probe 10, and the imaging region moves jointly with the ultrasound probe 10. By moving the ultrasound probe 10, the image region 22 is moved across the volume portion 2 so that the ultrasound image frames provide ultrasound images of various parts of the volume portion 2.

Here, an ultrasound image frame is defined as a two- or three-dimensional ultrasound image taken at a given time using the ultrasound probe. The image frame represents an entire image of a pre-defined size as acquired by the ultrasound probe. Subsequent image frames usually have the same resolution. In contrast, a dynamically selected subset of an ultrasound image frame, selected in dependence of the image content and possibly with variable size, is not an image frame. Typically, a time stamp is associated with the ultrasound image frame. The probe 10 collects the ultrasound image data as a data stream representing consecutive ultrasound image frames.

Figure 1B:
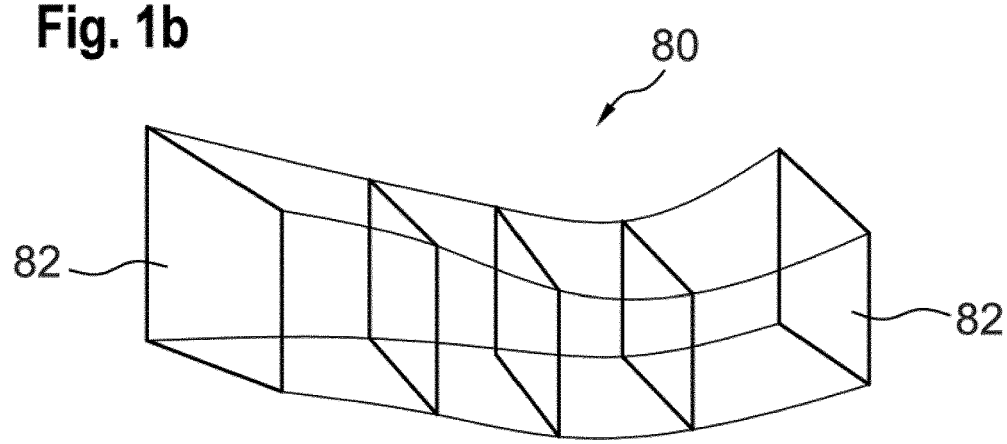

FIG. 1b shows one output of the proposed invention, a compounded three-dimensional ultrasound image. The compounded three-dimensional ultrasound image is a three-dimensional image indicating the ultrasound reflectivity properties in the scanned volume portion, obtained from the acquired ultrasound image frames and the determined movement (position and orientation) of the ultrasound probe 10 for each of the acquired ultrasound image frames 22. The compounded three-dimensional ultrasound image can, for example, be visualized as the set of the images frames positioned in space, or as a full 3D image, if further processed with a compounding algorithm such as the 3D reconstruction described further below.

Figure 1C:
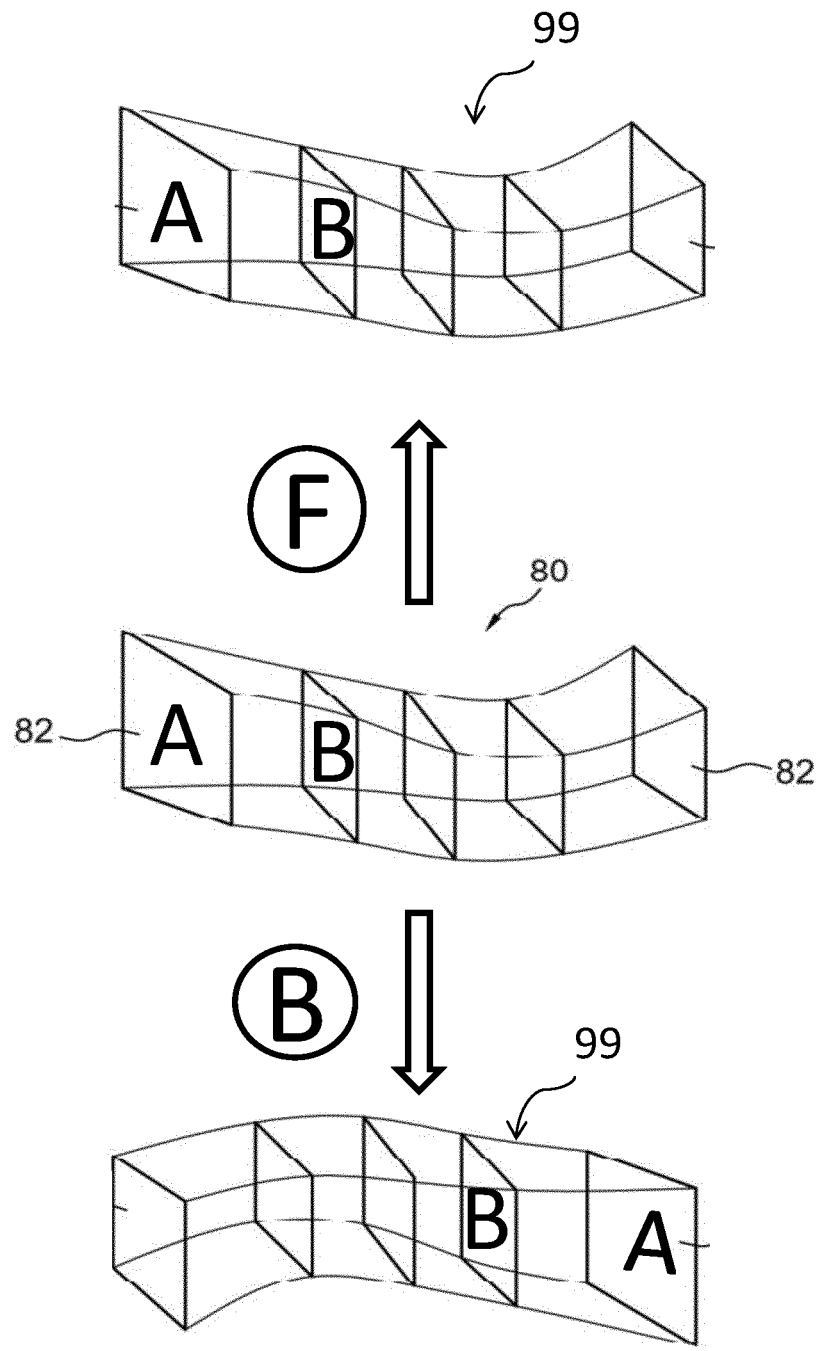
FIG. 1c shows schematically two options of forward-backward directedness for the compounded three-dimensional ultrasound image of FIG. 1b.

In the center of FIG. 1c the compounded three-dimensional ultrasound image of FIG. 1b is shown again, wherein two subsequent image frames A and B are indicated, wherein the ultrasound image frame B is shown to be on the "forward" side (in FIG. 1c to the right) of ultrasound image frame A. Generally, the forward and backward directedness indicates the directedness of the motion perpendicular to the image plane of the ultrasound probe. Thus, forward motion and backward motion are defined relative to the ultrasound probe. The ultrasound probe thus has a forward side on one side of the image plane (e.g., right side of the probe 10 relative to the image plane 22 in FIG. 1a), and a backward side on the other side of the image plane (e.g., left side of the probe 10 relative to the image plane 22 in FIG. 1a); and the forward or backward motion is a motion to the respective (forward or backward) side of the probe 10.

In the center of FIG. 1c the compounded three-dimensional ultrasound image already comprises an assumption whether the ultrasound image frame B is forward or backward (to the right or left) of ultrasound image frame A, i.e. whether the motion from ultrasound image frame A to ultrasound image frame B is a forward or a backward motion. Whether a motion goes forward or backward is described by the forward-backward directedness of the motion.

However, the forward-backward directedness shown in FIG. 1c has not been determined reliably. In other words, due to the inherent forward-backward symmetry of determining a motion from two consecutive ultrasound images, it may have been impossible to tell whether or not a motion is forward-backward flipped when considering two consecutive ultrasound image frames alone. In this case, the motion may have no (or just an arbitrary or default) forward-backward directedness, i.e. does not carry the information whether the motion is actually forward or backward. This type of motion, in which the forward-backward directedness is not necessarily determined, is also referred to as forward-backward directedness undetermined motion.

For determining the forward-backward directedness determined motion, it is proposed to obtain further information and combine this information with the information obtained from the ultrasound image in order to explicitly determine whether the motion from ultrasound image frame A to ultrasound image frame B is a forward motion F or a backward motion B, as indicated in the upper part or the lower part of FIG. 1c, respectively.

Figure 2:
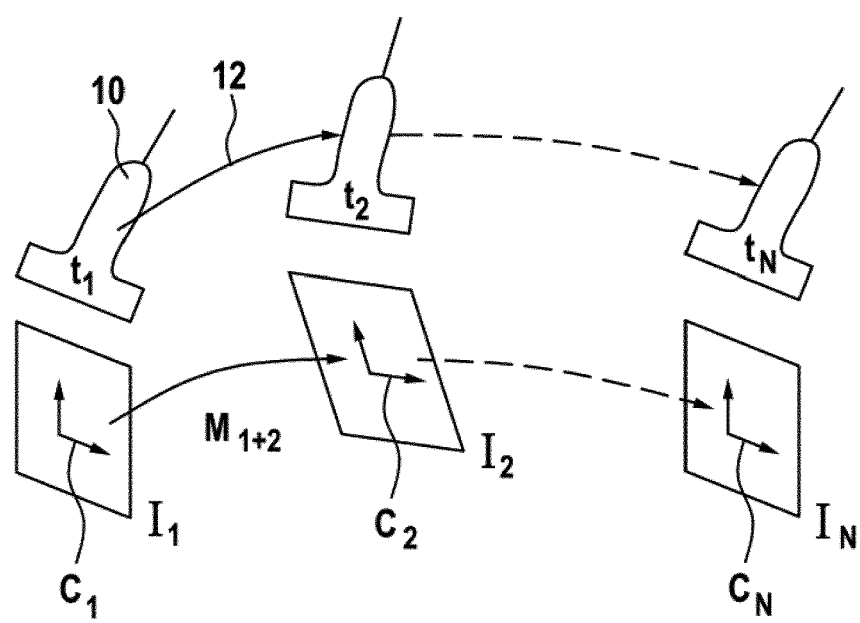

FIG. 2 depicts in more detail the challenging technical problem of obtaining the forward-backward directedness undetermined motion, which is one sub-problem that aspects of the invention aim at solving. During the acquisition, the ultrasound probe (10) is moved and the image content of the image frames 22 is therefore changing. An object of the present invention is to recover the motion of the probe 12 between two instants t1 and t2, using solely information from the image data I1 and I2 acquired at such times. The estimated motion can be represented as a matrix M12 that models the relative transformation between the coordinate system of one frame C1 and the coordinate system of the other frame C2. This process can then be repeated for the whole series of images.

Typically, the motion has six degrees of freedom (three translations and three rotations), and the matrix M12 can be parametrized by 6 parameters.

Figure 3B:
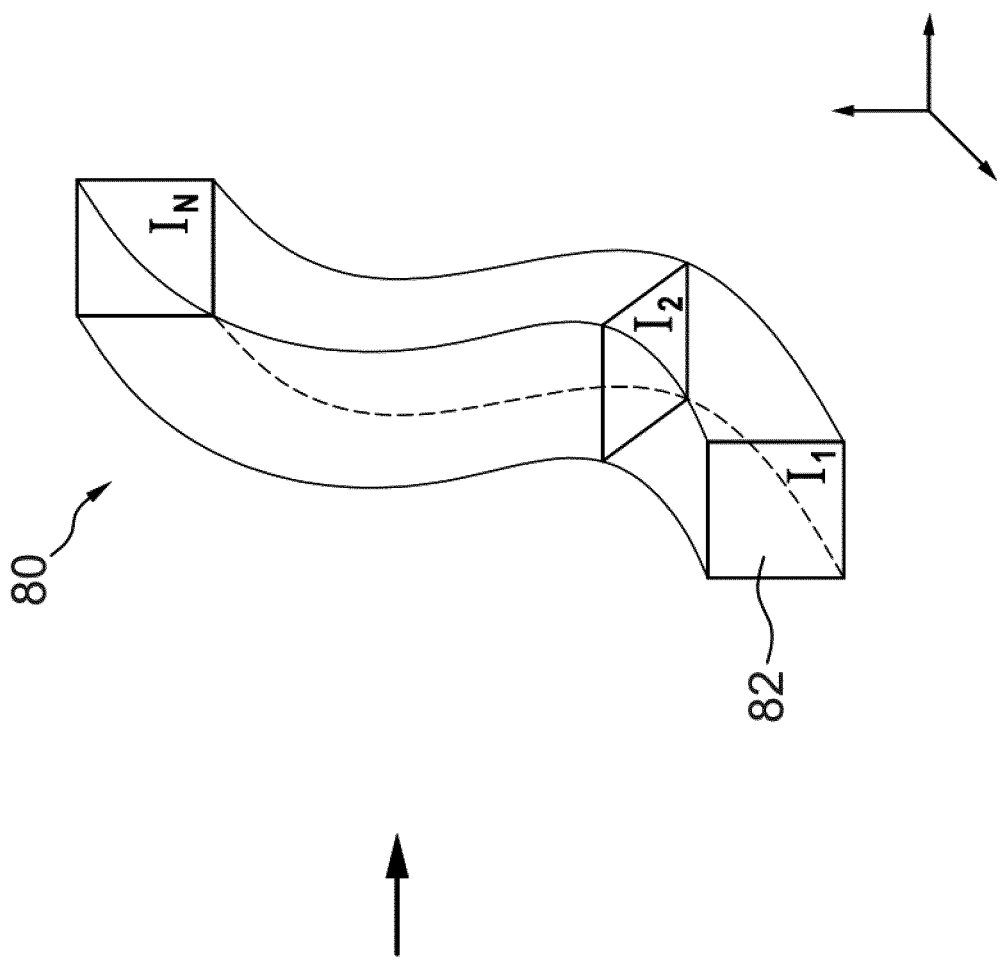
FIG. 3b shows schematically a compounded three-dimensional ultrasound image obtained by the method illustrated in FIG. 2
Figure 3A:
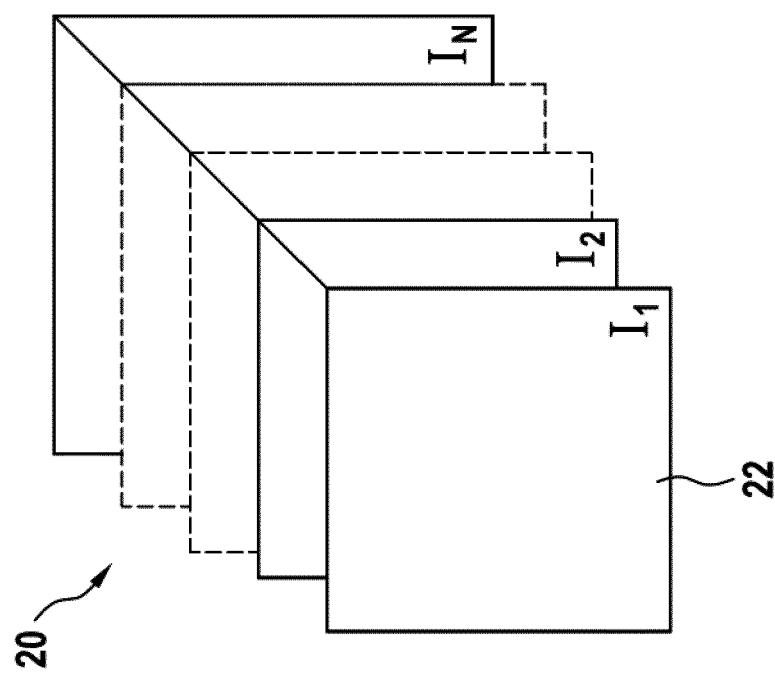
FIG. 3a shows schematically image data representing a plurality of ultrasound image frames, used as input in the method illustrated in FIG. 2.

FIG. 3a represents the input to the machine learning model 50, namely the ultrasound data 20 comprising a time series of ultrasound image frame data representing the ultrasound image frames 22 and corresponding time information (e.g., a time stamp or time index). In addition, the ultrasound data 20 may also comprise metadata, e.g., indicating ultrasound settings and/or presets such as gain, frequency, and/or dynamic range of the ultrasound image frames 22. The metadata may partially or fully be provided as a time series as well. In addition, the input to the machine learning model 50 may optionally include sensor data 24, e.g., a time series of sensor data and corresponding time information, as described in more detail with respect to FIG. 4a.

FIG. 3b corresponds to FIG. 1b and the description of FIG. 1b is also applicable to FIG. 3b.

Figure 4A:
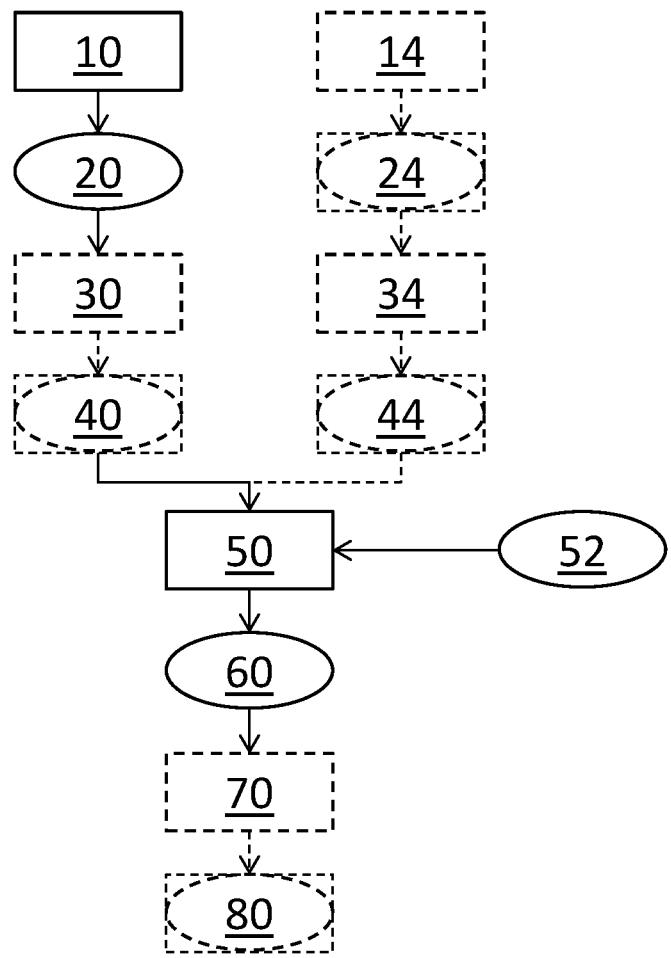
FIG. 4a shows schematically an apparatus for determining a three-dimensional motion of an ultrasound probe according to an embodiment of the invention.

FIG. 4a shows one part of the overall workflow of the proposed invention. Therein, optional steps are indicated with dashed lines. The main input of the system is the image data 20 generated by the ultrasound system 11 from the probe 10. Such images may be pre-processed with a variety of algorithms 30 like image resampling, image filtering or other high-level analysis. The pre-processed data 40 from multiple frames can then be input in a machine learning module 50 that is trained, from previous learning data 52, to produce an estimate 60 of the motion of the probe between the different input image frames. Such a process is repeated for all frames of the acquisition and the output of the machine learning model is then post-processed 70 to produce a trajectory of the probe 80.

The training from previous learning data 52 is performed before its utilization and comprises adjusting the values of the model parameters so that its output values are as close as possible to the expected values, as is known in the art. In other words, the training comprises solving a minimization problem for minimizing a deviation functional (e.g., L2 norm) with respect to the expected values.

Optionally, when an external sensor 14 is mounted on the ultrasound probe, its data 24 can also be pre-processed 34 and be used as additional input 44 of the machine learning module 50. To this purpose the data 24 is synchronized with the image data 20, e.g., by use of time stamps.

For the reasons discussed above, FIG. 4a thus describes a first submethod of the invention for determining a forward-backward directedness undetermined motion (which includes methods which assign a forward-backward directedness in a default or arbitrary manner, but not necessarily in a reliable manner).

Figure 4B:
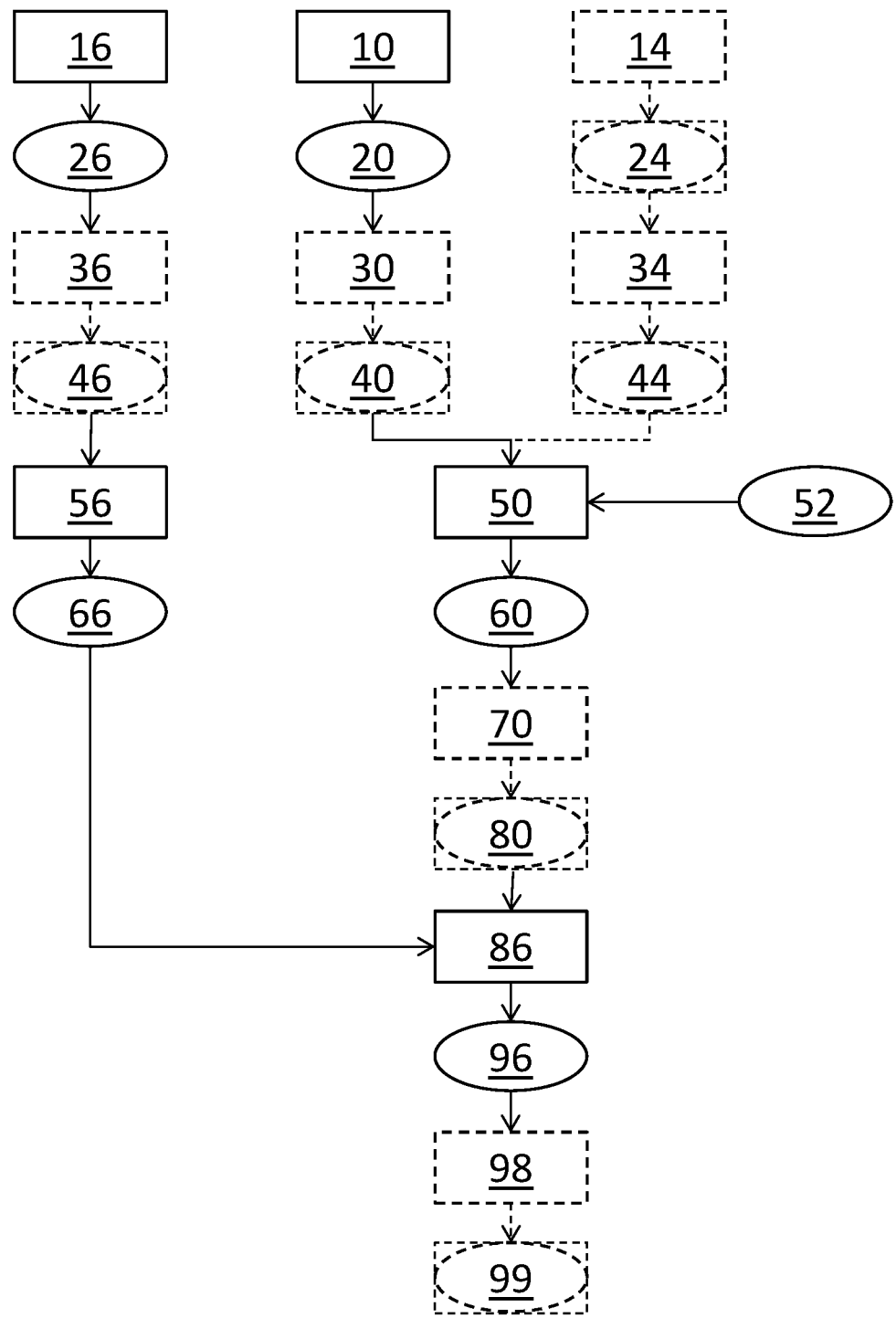
FIG. 4b shows schematically an apparatus for determining a three-dimensional directedness-determined motion of an ultrasound probe according to an embodiment of the invention.

Now turning to FIG. 4b, it is in the following described how the forward-backward directedness determined motion is obtained. FIG. 4b contains the method of FIG. 4a, described above, as a submethod. The result of this first submethod is combined with a second submethod possibly running parallel to the first submethod. The output of both submethods are combined in order to obtain a three-dimensional directedness-determined motion.

The main input of the second submethod is the directedness-indicative data 26 generated by a tracing system 16. Herein, the term "tracing system" is used for any system that generates directedness-indicative data 26, i.e., data not being agnostic to a forward-backward-symmetry. The tracing system 16 may, for example, be the external sensor 14 or an additional external sensor 18, as described in more detail with respect to FIGS. 9 and 10 below. Further, the directedness-indicative data can be received by the ultrasound probe 10 itself as described in more detail with respect to FIG. 11.

The directedness-indicative data 26 may optionally be pre-processed with a variety of algorithms 36.

The (pre-processed) directedness-indicative data 46 is then input in a directedness-determining system 56 described in more detail below. For example, the directedness-determining system 56 may include an algorithm calculating correlations between two data sets of the (pre-processed) directedness-indicative data 46 and/or an algorithm converting the (pre-processed) directedness-indicative data 26 to a binary variable. The directedness-determining system 56 may also be a second machine-learning module 58. The directedness-determining system 56 generates a directedness indicator 66, typically a binary variable having a first and a second value, e.g. "+1" and "−1", wherein the first value indicates a forward directedness of the motion and the second value indicates a backward directedness of the motion.

The directedness indicator 66 can be inputted into a determining module 86 using the information given by the directedness-undetermined estimate 60 of the motion (i.e., the three-dimensional (forward-backward directedness undetermined) motion) and the directedness indicator 66 in order to determine a directedness-determined motion indicator 96 estimating the motion of the probe between the different input image frames while simultaneously specifying the forward-backward directedness.

Usually, this process is repeated for all frames of the acquisition and the output of the machine learning model may then be post-processed 98 to produce the final trajectory of the probe 99. The determining module 86 can combine the information of the directedness indicator 66 with the trajectory of the probe 80 determined with the first submethod (cf. FIG. 4a), either before or after such post-processing.

Figure 5:
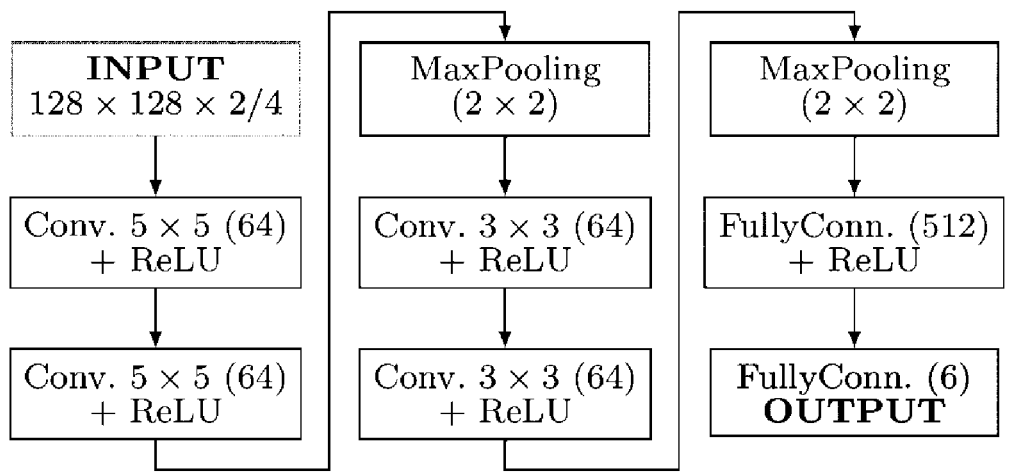
FIGS. 5 and 6 show schematically neural network architectures for a machine-learning module according to respective embodiments of the invention.

FIG. 5 represents an example of a (first) machine learning module 50 for use in embodiments of the invention, for the first sub-method of determining a motion indicator indicating a three-dimensional (forward-backward directedness undetermined) motion (e.g., to be used as the motion indicator 60 shown in FIG. 4b). The machine learning module 50 comprises a convolutional neural network. A two-channel image (representing two successive ultrasound frames) is the input of the neural network and goes through a series of convolutional layers (with 5×5 or 3×3 pixels kernels and 64 output channels), activation layers (here rectified linear units) and 2×2 pixels maximum pooling layers. At the end of the network, two fully connected layers aggregate the information from the whole features maps to a final output of six numbers representing 3 translations and 3 rotation parameters. These six numbers parametrize the matrix M12 mentioned above.

The parameters of the machine learning model (here the convolution kernels and the coefficients of the fully connected layers) are set as the final state of the training process. Given a set of training data (each training data sample can be composed of (i) a pair of successive ultrasound frames, and (ii) a very accurate estimate of the probe motion between those two frames, obtained for instance from a tracking system, and parameterized as six numbers), the training procedure can aim at minimizing the sum over all training data samples of the squared norm of the difference vector between the 6-dimensional output of the network and the 6 parameters of the actual measured probe motion. This minimization problem can be solved with a stochastic gradient descent or one of its variants like AdaGrad [John Duchi, Elad Hazan et Yoram Singer, «Adaptive subgradient methods for online learning and stochastic optimization», JMLR, vol. 12, 2011, p. 2121-2159] with a momentum of 90%, a batch size of 500 and no weight decay. The initial values of the network parameters can be randomly chosen, according to a Gaussian distribution with 0 mean and 0.01 standard deviation.

Optionally, an estimate of the in-plane translation can be pre-computed as the optical flow between the two images using known techniques (see article by Gunnar Farneback, cited further below). The output of this pre-computation of the optical flow is a 2D vector field that can be encoded as 2 additional optical flow channels. These 2 additional optical flow channels are used as additional input channels of the neural network (in addition to the 2 image channels described above).

Figure 6:
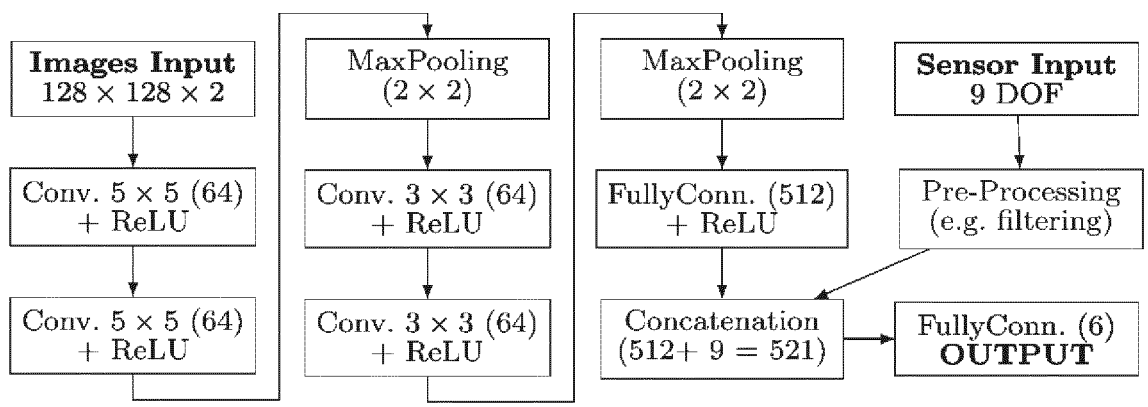

Similarly to FIG. 5, FIG. 6 represents an example of a neural network architecture that will take into account not only the image data but also some external IMU sensor information. The two architectures are mostly similar but the 9-dimensional measurements of the sensor are concatenated to the aggregated feature vector at the end of the network before producing the final output.

The method of FIG. 6, when taken alone, differs from the invention even if the additional sensor data may also allow a distinction between forward and backward motion. Contrary to the method of FIG. 6 taken alone, according to aspects of the invention the directedness-determined motion indicator is determined in a separate step (i.e. separately from determining the (directedness-undetermined) motion indicator), by combining the (directedness-undetermined) motion indicator with a separately determined directedness indicator. This aspect of the invention has the advantage that the machine learning problem of determining the (directedness-undetermined) motion indicator is unburdened from the task of breaking the forward-backward ambiguity with additional sensor data. As a result, the machine learning algorithm can produce more reliable results from a given amount of training data.

Next, test results of an example implementation according to an aspect of the invention, compared to prior art implementations, are discussed. For obtaining these test results, the set up described in the following was used.

Datasets acquisition and baseline methods: All sweeps used in the example implementations were captured with a Cicada-64 research ultrasound machine by Cephasonics (Santa Clara, CA USA). Therein, a linear 128-element probe was used. The probe was tuned at 9 MHz for generating the ultrasound images. The depth of all images was set to 5 cm (with a focus at 2 cm) and 256 scan-lines were captured per image.

The B-mode images were used without any filtering or back-scan conversion, resampled with an isotropic resolution of 0.3 mm. The probe was equipped with an optical target which was accurately tracked by the tracking system Stryker Navigation System III.

Using this tracking system, and after spatial and temporal image-to-sensor calibration, the inventors were able to obtain a ground truth transformation with absolute positioning accuracy of around 0.2 mm. It was also assured the temporal calibration exhibits neither jitter nor drift at all, thanks to the digital interface of the research US system and proper clock synchronization. Thus, the ground truth had sufficient precision from frame-to-frame.

The experiments were based on three datasets:
 a set of 20 US sweeps (7168 frames in total) acquired on a BluePhantom ultrasound biopsy phantom. The images contain mostly speckle but also a variety of masses that are either hyperechoic or hypoechoic;
 a set of 88 in-vivo tracked US sweeps (41869 frames in total) acquired on the forearms of 12 volunteers. Two different operators acquired at least three sweeps on both forearms of each participant;
 another 12 in-vivo tracked sweeps (6647 frames in total) acquired on the lower legs on a subset of the volunteers. This last set was used to assess how the network generalizes to other anatomies.

All sweeps have been acquired in a fixed direction (proximal to distal). Applying the algorithm on a reversed sweep would yield a mirrored result. However, the method according to the present invention is not limited to any specific sweeping direction.

The algorithm according to the present invention was compared to two comparative methods:
 linear motion, which is the expected motion of the operator in the sweeping direction. This means all parameters are set to their average value over all acquisitions: rotations and in-plane translations are almost zero while elevational translation $t_z$ is constant around 2 cm/s;
 speckle decorrelation method, according to the current state of the art: In this comparative method, each image was filtered to make the speckle pattern more visible as described in Afsham, N., Rasoulian, A., Najafi, M., Abolmaesumi, P., Rohling, R.: Nonlocal means filter-based speckle tracking. IEEE transactions on ultrasonics, ferroelectrics, and frequency control 62(8) (2015) 1501-1515. Then, each image was divided in 15×15 patches, and the corresponding patch-wise cross-correlations were computed. Then, a standard exponential-based model was computed to deduce the corresponding z-displacement from the correlation values. Finally RANSAC was used to compute a robust fit of the 6 transformation parameters to the displacement field. These method steps are described in Prager, R. W., Gee, A. H., Treece, G. M., Cash, C. J., Berman, L. H.: Sensorless freehand 3-d ultrasound using regression of the echo intensity. Ultrasound in medicine & biology 29(3) (2003) 437-446.

These comparative methods were compared to two implementations of embodiments of the present invention: The first implementation, referred to as "standard CNN" uses the convoluted neural network approach as described with reference to FIG. 5 above, with two input fields (two images between which the relative motion is to be determined). The second implementation, referred to as "CNN with optical flow", differs from the "standard CNN" in that it further uses the pre-computed optical flow, and therefore uses a total of four input fields as described with reference to FIG. 5 above.

For each of these methods and datasets, the three-dimensional motion indicators (three translations $t_x$, $t_y$, $t_z$, and three rotations $\theta_x$, $\theta_y$, $\theta_z$) were computed. Further, error metrics on these parameters were computed by comparing them with the data from the above-described tracking system. The parameter-wise errors were computed and averaged for every frame with respect to the first frame of the sweep. Further, a final drift, defined as the distance between the last image center with the estimated tracking and ground truth, was computed.

The results are summarized in the tables 1-3 below:

TABLE 1

| phantom dataset | avg. absolute error (mm/°) | | | | | | final drift (mm) | | |
|---|---|---|---|---|---|---|---|---|---|
| | $t_x$ | $t_y$ | $t_z$ | $\theta_x$ | $\theta_y$ | $\theta_z$ | min | med. | max |
| linear motion | 2.27 | 8.71 | 38.72 | 2.37 | 2.71 | 0.97 | 2.29 | 70.30 | 149.19 |
| speckle decorrelation | 4.96 | 2.21 | 29.89 | 2.10 | 4.46 | 1.93 | 12.67 | 47.27 | 134.93 |
| standard CNN | 2.25 | 5.67 | 14.37 | 2.13 | 1.86 | 0.98 | 14.31 | 26.17 | 65.10 |
| CNN with optical flow | 1.32 | 2.13 | 7.79 | 2.32 | 1.21 | 0.90 | 1.70 | 18.30 | 36.90 |

TABLE 2

| forearms dataset | avg. absolute error (mm/°) | | | | | | final drift (mm) | | |
|---|---|---|---|---|---|---|---|---|---|
| | $t_x$ | $t_y$ | $t_z$ | $\theta_x$ | $\theta_y$ | $\theta_z$ | min | med. | max |
| linear motion | 4.46 | 6.11 | 24.84 | 3.51 | 2.59 | 2.37 | 10.11 | 46.23 | 129.93 |
| speckle decorrelation | 4.36 | 4.09 | 18.78 | 2.53 | 3.02 | 5.23 | 9.19 | 36.36 | 98.95 |
| standard CNN | 6.30 | 5.97 | 6.15 | 2.82 | 2.78 | 2.40 | 3.72 | 25.16 | 63.26 |
| CNN with optical flow | 3.54 | 3.05 | 4.19 | 2.63 | 2.52 | 1.93 | 3.35 | 14.44 | 41.93 |
| after speckle filtering | 3.57 | 3.59 | 8.56 | 2.56 | 2.64 | 2.01 | 5.14 | 22.04 | 44.15 |

TABLE 3

| lower legs dataset | avg. absolute error (mm/°) | | | | | | final drift (mm) | | |
|---|---|---|---|---|---|---|---|---|---|
| | $t_x$ | $t_y$ | $t_z$ | $\theta_x$ | $\theta_y$ | $\theta_z$ | min | med. | max |
| linear motion | 4.49 | 4.84 | 39.81 | 4.39 | 2.18 | 2.46 | 37.35 | 73.40 | 143.42 |
| speckle decorrelation | 5.02 | 2.87 | 30.89 | 1.82 | 1.78 | 4.11 | 43.21 | 54.74 | 89.97 |
| standard CNN | 5.34 | 5.62 | 17.22 | 2.58 | 2.45 | 2.84 | 21.73 | 43.21 | 65.68 |
| CNN with optical flow | 4.14 | 3.91 | 17.12 | 1.94 | 2.58 | 2.15 | 25.79 | 40.56 | 52.72 |
| CNN trained on legs | 3.11 | 5.86 | 5.63 | 2.75 | 3.17 | 5.24 | 8.53 | 19.69 | 30.11 |

When comparing the above methods, it can be seen that the linear motion method gives the worst results of the four methods, mainly due to the out-of-plane translation $t_z$. This is expected since keeping a constant speed is difficult, so that this component is expected to have the largest variability. The speckle decorrelation method significantly reduces all estimation errors by exploiting the correlations between the frames; nevertheless the out-of-plane error on $t_z$ and therefore the overall drift is still quite high.

On the other hand, the standard CNN method (without optical flow channels) is able to produce results that are already better than the comparative examples. One can notice, however, that the $t_x$ and $t_y$ errors are somewhat high, especially on the forearm sweeps. This error may be reduced by additional training data allowing the system to learn the whole transformation more accurately by a larger dataset. This problem is also much reduced by adding the optical flow as input channels (CNN with optical flow method). Indeed, for the CNN with optical flow method, $t_x$ and $t_y$ for instance are estimated more accurately; and the estimation of $t_z$ is even further improved.

As a result, we observe on real clinical images a final drift of merely 1.45 cm over sequences longer than 20 cm, which is twice as accurate as the comparative examples. The hierarchy of the methods (from low to high accuracy: linear; speckle decorrelation; standard CNN; CNN with optical flow) was confirmed by paired signed-rank Wilcoxon tests which all yielded p-values lower than $10^{-6}$.

Next, the influence of noise filtering is discussed. In order to test the importance of the speckle noise, we compared the methods when applied on the images before and after applying the speckle filter built in the Cephasonics ultrasound system. As we can see in the last row of Table 2 above, learning and testing on the unfiltered images yields better tracking estimation. This shows that speckle patterns are important for the neural network, in particular for the estimation of the out of plane translation. On the other hand, the CNN methods on filtered images already give better results than the comparative methods. Thus, it can be concluded that speckle is indeed highly useful, but not strictly necessary for estimating out-of-plane motion.

Generalization to other anatomies: Another interesting question is how well the machine learning approach can generalize to other applications: does it really learn the motion from general statistics, or does it overfit to some anatomical structures present in the image?

The results are reported in Table 3 above. Here, the training data was based on a forearm dataset, but the results are reported for a lower leg dataset. Compared to Table 2, these results show a significant degradation of the accuracy for all methods. For the comparative methods, this is due to incorrect calibration (since they have been calibrated on the forearms dataset). For the methods according to the invention, the degradation is even more severe (since they have been learned on the forearms dataset). In more detail, the in-plane displacements are still recovered with a reasonable accuracy, but the error on the out-of-plane translation $t_z$ has strongly increased.

However, the methods according to the invention still generalize better than the others to new kind of images. This preliminary experiment shows that the accuracy is strongly dependent on the target anatomy but gives hope regarding the capabilities of machine-learning approaches.

For comparison, in the last row of Table 3, we also report the accuracy obtained with a CNN trained on this specific dataset, which is only slightly worse than on forearms (due to the smaller size of the dataset).

Next, FIG. 7 is discussed. Here, the same methods discussed above for Tables 1-3 have been used. For testing the out-of-plane estimation under challenging environments, the predictions by these methods is shown for a separate sweep with a deliberately strongly varying speed: The first 100 and last 150 frames were recorded at an average speed of 0.3 mm/frame, while inbetween the speed has almost been doubled. FIG. 7 shows the different predictions of the elevational translation.

As might be expected, the linear motion method assumes a constant speed and will therefore yield major reconstruction artifacts. The speckle decorrelation approach does detect a speed change but strongly underestimates large motions. Only the methods according to embodiments of the invention are able to follow the probe speed accurately.

A qualitative comparison of the reconstructed trajectories on a sample sweep is shown in FIGS. 8a-8c. Specifically, FIGS. 8a-8c show respective 3D visualizations of tracked ultrasound sweeps. The ultrasound frames have been displayed with their ground truth position and their trajectory are emphasized with the black contour. In comparison, the outline of the trajectories obtained with the other methods are also shown in other colors: red for the linear motion method, blue for our implementation of the speckle decorrelation method and green for our proposed method based on deep learning.

FIG. 8a represents a median case in terms of performance (more particularly final drift) for our method, FIG. 8b corresponds to the best case and FIG. 8c the worst case over the tested forearms dataset. They highlight the hierarchy of the different methods in terms of tracking estimation accuracy.

Further examples of test results of example implementations according to aspects of the invention can be found in the publication "3D freehand ultrasound without external tracking using deep learning", in: Medial Imaga Analysis (August 2018), Volume 48, Pages 187-202, retrieveable at http://doi.org/10.1016/j.media.2018.06.003, which is hereby incorporated in its entirety by reference.

Further details regarding this approach are also described in R. Prevost et al., "Deep Learning for Sensorless 3D Freehand Ultrasound Imaging", in: M. Descoteaux et al. (Eds.), MICCAI 2017, Part II, LNCS 10434, pp. 628-636, 2017, DOI: 10.1007/978-3-319-66185-8_71, which is hereby incorporated in its entirety by reference.

Figure 9:
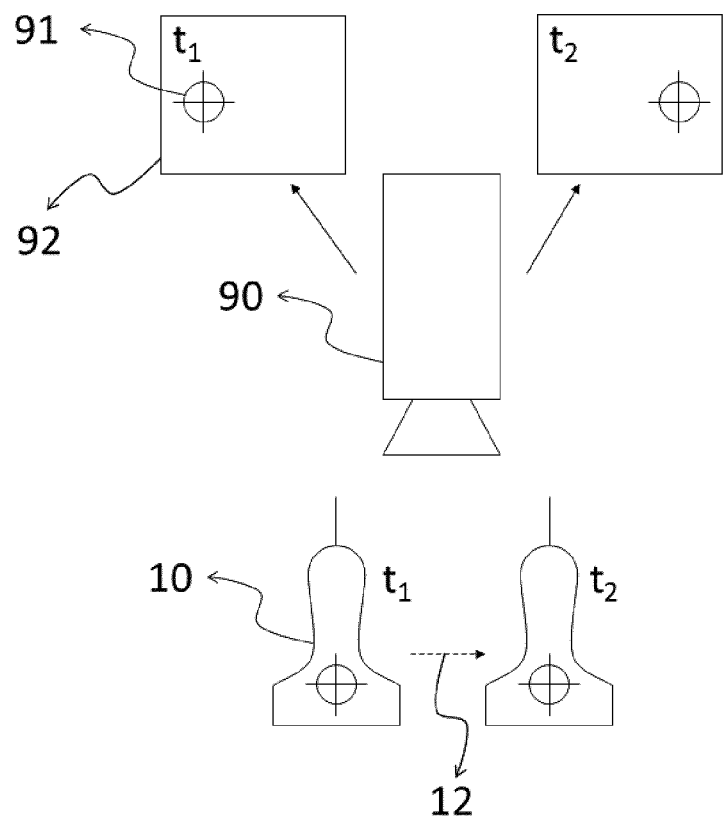
FIG. 9 shows schematically an optical tracking system tracking a position of the ultrasound probe in order to receive directedness-indicative data.
Figure 10:
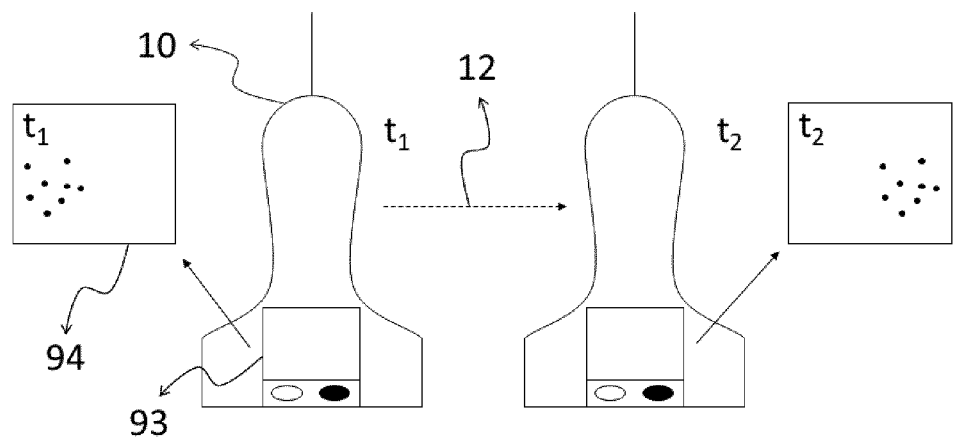
FIG. 10 shows schematically an optoelectronic sensor attached to the ultrasound probe in order to receive directedness-indicative data.
Figure 11:
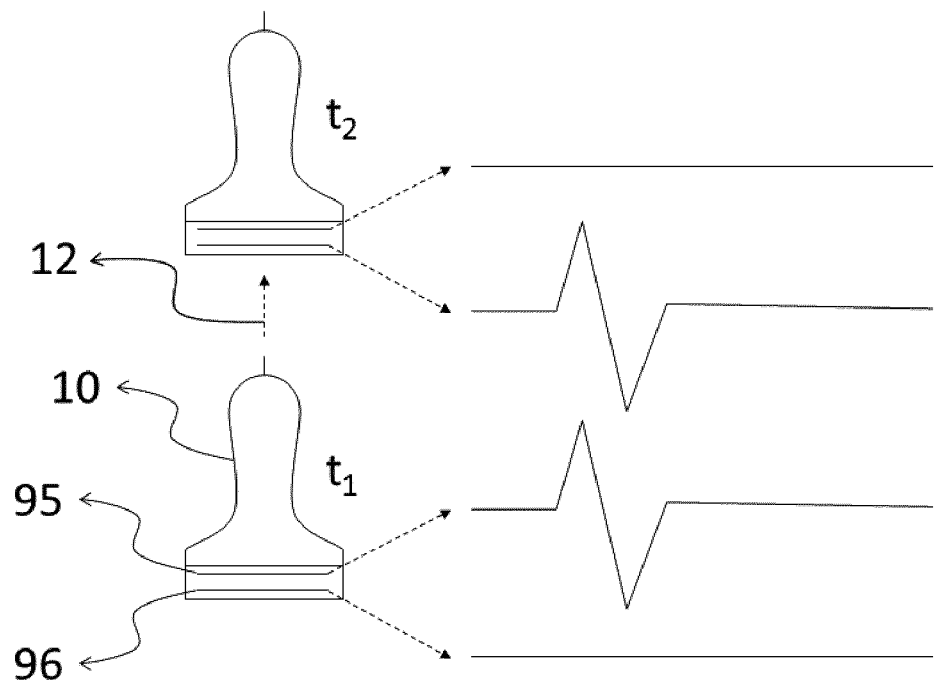
FIG. 11 shows schematically a multi-row ultrasound array used to receive directedness-indicative data.

Next, with reference to FIGS. 9 to 11, example methods for determining the forward-backward directedness of the motion 26. Any of these methods can be implemented by the tracing system 16 for generating the forward-backward directedness indicator 66 illustrated in FIG. 4b. This forward-backward directedness indicator 66 can subsequently be combined (multiplied) with the motion indicator 60 (see FIG. 4b), to obtain the final directedness-determined three-dimensional motion.

FIG. 9 shows an (optical) tracking system used as the tracing system. This method may for example use an optical camera in combination with a marker or marker set. The marker set may be dedicated markers. Alternatively, the marker set may be general features or landmarks in the camera's field of view allowing a general feature tracking by pattern recognition/tracking including, in particular, a skin feature tracking. In addition, the ultrasound probe itself or at least a part of the ultrasound probe may be or comprise the marker set. For example, as shown in FIG. 9, the camera can be stationary tracking a marker set fixed to the ultrasound probe. In this example, the probe 10 is equipped with a marker 91, and a camera 90 tracks the motion and orientation of the probe 12, capturing two images 92 at different time points. Alternatively, the camera may be attached to the ultrasound probe and being configured to track marker sets in its environment. FIG. 9 shows one option of tracking the motion of the probe with an optical camera and a marker on the probe.

After calibrating the camera and knowing the viewing angle of the camera, a motion (and orientation) of the marker pattern between the subsequent images acquired by the camera can be obtained by known methods. Together, this motion and orientation allow to determine whether the ultrasound probe is moving forwards or backwards. Thus, the required forward-backward directedness of the motion (e.g. a positive or negative overall sign) can be determined.

In another embodiment, the camera can be attached to the ultrasound probe facing the environment and tracking a fixed marker set in the environment. A camera facing the environment may be configured to detect the marker set in the environment and to use a Simultaneous Localization and Mapping (SLAM) method, in order to determine the forward-backward directedness of the motion of the ultrasound probe. Tracking the forward-backward directedness of the motion with an optical tracking system may be advantageous due to its relative ease of implementation and use.

Another method to determine the forward-backward directedness of the motion comprises usage of an accelerometer. The accelerometer can be included in an IMU sensor, including a combination of accelerometers and gyroscopes. In order to determine the forward-backward directedness of the motion an algorithm can determine the directedness of the acceleration. An integration over time gives the velocity. By integration of the accelerometer signals the noise can be reduced by averaging out fluctuations. Incremental calculations such as this tend to accumulate error over time, so the velocity data may periodically be reset and/or calibrated using other data, such as data from the ultrasound images or from sensors such as a gyroscope. In order to perform numerical integration, an initial velocity is required. The initial velocity can be assumed to be zero, i.e. starting the motion of the ultrasound probe from rest, or, for example, can be obtained from the first submethod. For example, the velocity can be set to zero under the condition that the magnitude of the movement determined from the first submethod is below a predetermined threshold. Instead of a straightforward integration it is also possible to do Kalman filtering.

FIG. 10 shows one method to determine the forward-backward directedness of the motion using an external sensor detecting a one- or two-dimensional motion relative to an underlying surface, e.g. the skin of a patient. One such sensor can be an optoelectronic sensor. The optoelectronic sensor is usually used in combination with an illumination source or light emitter, particularly a LED or LASER. FIG. 10 represents an example method to determine the forward-backward directedness of the motion using an optoelectronic sensor. An optoelectronic sensor 93 may be attached to the ultrasound probe 10. The optoelectronic sensor continually projects a pattern on to the underlying surface and it acquires low-resolution images 94 of this projection. By subsequently acquiring low-resolution images 94 of the underlying surface together with an illumination source during movement of the probe 12, the optoelectronic sensor can determine the forward-backward directedness of the motion by any algorithm known for, e.g., determining the motion of a computer mouse.

Any other sensor used for a computer mouse may be used in an analogous manner for determining the one- or two-dimensional surface motion relative to an underlying surface. Examples include a sensor for determining this surface motion by detecting the angular motion of a rotating element such as a sphere or a wheel. Such a sensor can be an odometer or a rotary encoder, for example. An odometer usually determines mechanically and/or electronically a covered distance and may provide a digital output signal. A rotary encoder converts the angular position or motion of a rotating element digital output signal as well. The rotary encoder may be electronic, mechanical, optical, magnetic, capacitive or a combination thereof. The rotary encoder might be an incremental or absolute encoder. The rotating element may be attached to the ultrasound probe such that it is driven in rotation by the motion of the ultrasound probe, e.g. due to the contact to the underlying surface, i.e. by sliding over the underlying surface. The forward-backward directedness of the motion of the ultrasound probe influences the rotational direction of the rotating element sliding on the underlying surface. Depending on the rotational direction the corresponding digital signal sent out by the rotary encoder allows determination of the forward-backward directedness of the motion.

FIG. 11 shows another method to determine the forward-backward directedness of the motion using an ultrasound probe with a multi-row ultrasound array. In general, a multi-row ultrasound array may improve accuracy for tracking. The usage of a multi-row ultrasound array probe 10 allows the determination of the forward-backward directedness directly from the ultrasound image data and does not require additional hardware. In FIG. 11, a multi-row ultrasound array probe 10 is moved over the underlying surface in the movement direction 12 and acquiring raw ultrasound signals. In order to obtain the signals from different transducer rows of the array access to raw IQ data is necessary, in particular raw channel data may be required.

FIG. 11 shows a simple situation which illustrates the fact that multiple rows of ultrasound images from a multi-row ultrasound array probe 10 contain sufficient information for determining the forward-backwards directedness of the motion: In the situation of FIG. 11, at time t1 the probe 10 detects an echo at the transducer row 95*a* and no signal on transducer row 95*b*; and at a later time t2, the same echo is detected by transducer row 95*b*, with transducer row 95*a* receiving no echo signal from the volume portion. This indicates that the ultrasound probe as moved over the tissue in such a manner that a tissue portion causing the echo signal was at time t1 at the transducer row 95*a*, and at time t2 at the transducer row 95*b*. In other words, because the relative position and orientation of the transducer rows 95*a*, 95*b* in the ultrasound probe are known, it can be determined from the ultrasound images that the probe moved upwards in FIG. 11. In case the order of the signals received by the transducer rows would be reversed, the opposite forward-backward directedness, i.e. the opposite sign, of the motion would be observed.

Figure 12:
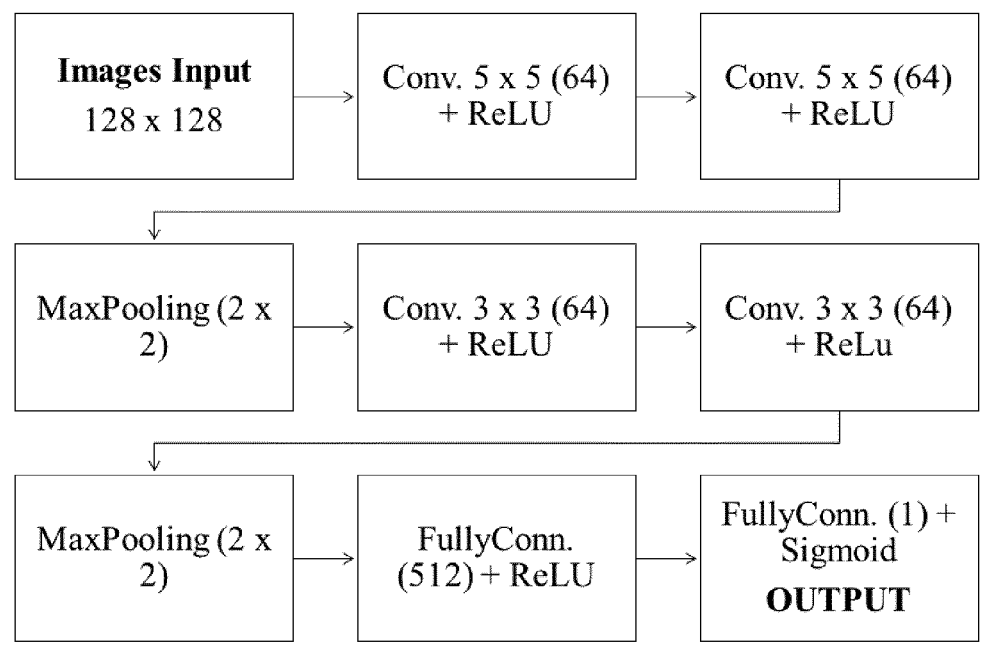
FIG. 12 shows schematically a neural network architecture for a second machine-learning module for determining the forward-backward directedness of the motion according to respective embodiments of the invention.

More generally, by calculating the correlation of the signal received at time t1 by a first transducer row 95*a* and the signal received at time t2 by transducer row 95*b*, a correlation between signals coming from the same spot on an underlying surface may be detected; and from this correlation a forward-backwards directedness of the motion may be determined (e.g., by a further machine-learning module analogous to the one shown in FIG. 5 or 6 or 12, trained to determine the forward-backwards directedness indicator).

FIG. 12 shows a second machine learning module 58 (see FIG. 4*b*) for use in embodiments of the invention. Similar to the first machine learning module 50 of FIG. 5 or 6, the second machine learning module 58 may use a large set of the ultrasound image data received by the ultrasound probe 10 as an input, e.g., at least five ultrasound image frames, preferably spanning a major portion (more than 50% of the length in forward-backward direction) of the total volume across which image compounding is to be performed. With this data, the second machine-learning module 58 may be trained to determine a forward-backward directedness of a motion.

Different from the first machine learning module 50 of FIG. 4*b* (e.g., implemented according to FIG. 5 or 6), the input data of the second machine learning module 58 has information about the forward-backward directedness of the motion, because it contains not only a few (two or three) ultrasound images, but a plurality of images spanning a large volume containing information about anatomical characteristics of the human body. For example, when an ultrasound probe is moved from the hand to the shoulder, the wrist bones are seen before the humerus bone in the ultrasound image frames. Hence, the machine-learning module 58 can learn to identify the forward-backward directedness between the image frames by identifying wrist bones for or after a humerus bone.

In general, the training of the second machine learning module 58 of FIG. 4*b* using sequences of ultrasound images acquired on human bodies, containing specific characteristics accompanied with the human anatomy which indicate a forward or backward directedness. Again, the use of the second machine learning module of FIG. 11 is very different from the approach illustrated in FIG. 6 alone. By having two separate (i.e., first and second) machine learning modules, separately determining the (directedness-undetermined) motion indicator and the directedness indicator, the machine learning problem of determining the (directedness-undetermined) motion indicator by the first machine learning module is unburdened from the task of breaking the forward-backward ambiguity and, as a result, may produce more reliable results from a given amount of training data.

Preferably, the second machine learning module 58 may comprise a neural network, preferably a convolutional neural network. A neural network model which could be used to determine the missing forward-backward directedness of a motion by using known anatomical information can have architecture as shown in FIG. 12. The input of this network would consist of a sequence of N subsequently acquired ultrasound images from the ultrasound probe (i.e. ultrasound video). It uses similar elements to the network in FIG. 5 or 6 such as convolutional layers and pooling layers as well as fully connected layers together with the ReLU and sigmoid nonlinearities. Additionally, recurrent layers such as an LSTM layer could be used in combination with convolutional layers, making use of the sequential nature of the data. As the sequence of ultrasound images is acquired on human anatomy used to train the network and because human anatomy exhibits certain directionality, e.g. branching of the blood vessels during motions leading away from the heart, the network is able to determine the forward-backward directedness of a motion of the probe from the image sequence. The output from this model may consist of a binary variable describing either the forward or the backward directedness of the movement. Usually, such an approach will require post-processing as the determination of the forward-backward directedness will be much more accurate with the whole stream of ultrasound image data compared with an estimation received with, for instance, only two successive ultrasound image frames.

Description of Further Aspects:

Next, various more general aspects of the invention are defined in more detail. Each aspect so defined may be combined with any other embodiment or with any other aspect(s) unless clearly indicated to the contrary. Reference signs referring to the Figures are for illustration only, but are not intended to limit the respective aspect(s) to the embodiments shown in the Figures.

According to an aspect, a three-dimensional motion of the ultrasound probe 10 is determined. According to an aspect, the three-dimensional motion has six degrees of freedom and includes a displacement (three degrees of freedom) and a rotation (three degrees of freedom). The displacement comprises in-plane displacements and elevational displacement; the rotation comprises in-plane rotation and out-of-plane rotations. Here, the terms in-plane and out-of-plane refer to an image plan defined by the image frame 22 acquired by the ultrasound probe 10. The three-dimensional motion indicator may be any parametrization of these degrees of freedom, or at least of a subset of these degrees of freedom. According to an aspect, the ultrasound probe is a free-hand probe and has the full six degrees of freedom. According to another aspect, the ultrasound probe is subject to constraints limiting the degrees of freedom to less than six.

The method includes receiving a stream of ultrasound image data from the ultrasound probe 10, and inputting at least a sub-set of the ultrasound image data representing a plurality of ultrasound image frames into a machine-learning module. The (sub-set of) ultrasound image data may be pre-processed, filtered or altered in any other manner. The term "at least a sub-set" requires that the information contained in the ultrasound image data from the ultrasound probe is at least partially input into the machine-learning module.

According to an aspect, even the full image data or a subset thereof is taken as the input subset. In case of a subset, the subset is taken irrespective of the image content of the ultrasound image frames and does therefore not require any image analysis.

Next, aspects relating to pre-processing of the ultrasound image data are described. According to an aspect, the method comprises pre-processing of the ultrasound image data before at least the subset of the ultrasound image data is input to the machine-learning module. For example, the pre-processing may include pre-computing a motion-indicative data. An example of motion-indicative data is the in-plane displacement data representing the in-plane displacement between the at least two of the ultrasound images. The method may then comprise inputting the motion-indicative data (such as the in-plane displacement data) as an additional input to the machine learning module. For example, motion-indicative data may be a two-dimensional data set such as a vector field, and may be input to the machine learning module as an additional image channels.

An advantage of this aspect is that by inputting to the machine-learning module data representing explicitly some easily calculable aspects of the motion, the machine-learning module may be enabled to provide information on the remaining aspects more reliable and/or with fewer training data.

The pre-computing of the in-plane displacement may be carried out by any known method. According to an aspect, the pre-computing is carried out by an "optical flow" method such as the one described in [Gunnar Farneback, Two-frame motion estimation based on polynomial expansion, Lecture Notes in Computer Science, 2003, (2749), 363-370]. Thus, the in-plane displacement data may be computed as an optical flow vector field representing a sub-pixel dense optical flow between the at least two ultrasound images.

According to a further aspect, the ultrasound image data can be pre-processed using at least one of the following:

Resampling: The ultrasound image data may be resampled to a given size or such that each of its pixels has a given resolution. This is done to make the system robust to some settings of the ultrasound system (like the depth or the number of scanlines used).

Image Filtering: This includes any local filters (like low-pass or high-pass filters), adaptive filters (like speckle denoising, enhancing or masking) or global image transformation (like histogram equalization).

Segmentation: Another pre-processing would consist in segmenting the image, i.e. classifying all pixels as one of multiple classes and using such probability maps as additional inputs. In a medical application for instance, an example would be to segment the skin, the fat, the muscle and the bone pixels.

Any pre-computed feature: For instance, as described before, use as the optical flow vector field as additional channels for the model input According to a further aspect, if additional sensor data is input, the sensor data can be pre-processed using at least one of the above.

According to an alternative aspect, no pre-processing of the ultrasound image data takes place before at least the subset of the ultrasound image data is input to the machine-learning module.

Next, aspects relating to the machine learning module are described. According to an aspect, the machine learning module comprises a neural network. In particular, the machine learning module may comprise a convolutional neural network.

According to a further aspect, the convolutional neural network has a convolutional layer outputting a plurality of feature maps, each feature map being the result of a convolution with a particular kernel of the layer input. Throughout the present application, the indefinite article "a" is used in the sense of "at least one", and in particular includes the possibility of a plurality. The convolutional neural network may have a plurality of convolutional layers, e.g., two, three or four convolutional layers, connected to each other in series and optionally with a pooling layer between at least some of the convolutional layers.

According to a further aspect, the convolutional neural network also includes an activation layer (for instance a sigmoid or a rectified unit layer) and/or a fully connected layer that outputs either a global feature vector or the final prediction of the network. The convolutional neural network may, for example, comprise a plurality of (e.g. two) fully connected layers receiving input from the convolutional layer(s) and/or pooling layer(s), and providing as an output the motion data (e.g., six numbers representing 3 translations and 3 rotation parameters).

According to a further aspect, the neural network is a recurrent neural network having a dynamic temporal behavior (i.e. the prediction of the network for a given ultrasound image data depends on the previous frames that have been inputted in the network). One popular architecture choice is for instance the long short-term memories (LSTM) networks.

Although the machine learning module according to the invention has been mainly illustrated by a neural network, it is not limited to neural networks. Instead, other types of machine learning module may also be used. For example, according to a further aspect, the machine learning module may also include for example a random forest algorithm.

Next, aspects relating to further details of input data from the ultrasound probe are described.

According to an aspect, the method comprises inputting local image data corresponding to a pair (or subset) of (consecutive) image frames to the machine learning module for determining the relative three-dimensional motion between the pair (subset) of ultrasound image frames, and repeating this process for consecutive pairs or subsets of image frames.

According to an alternative aspect, the method comprises inputting a global set of image data substantially spanning the whole set of image frames to the machine learning module for determining the relative three-dimensional motion between a first one and a last one of the ultrasound image frames. Thus, for example the full stream of the ultrasound image data may be input into the machine-learning module.

According to a further aspect, the method may include skipping a frame such as each second frame. Thereby the demands on computing power may be reduced while still providing timely information.

According to a further aspect, the method may comprise inputting to the machine learning module a global set of image data substantially spanning the whole set of image frames. Then, the machine learning module may determine the relative three-dimensional motion between some ultrasound image frames such as a first one and a last one of the ultrasound image frames.

According to a further aspect, the image data is two- or three-dimensional, i.e. it describes two-dimensional image frames or a three-dimensional image frames. For example, three-dimensional image frames may be produced by using a probe capable of imaging small 3D ultrasound volumes, e.g. by a matrix array ultrasound transducer or by a wobbler ultrasound system.

According to a further aspect, the image data may include data obtained by at least one ultrasound imaging modes such as A-Mode, B-Mode, continuous harmonic imaging, color-Doppler mode, Plain wave imaging or the like. According to a further aspect, the image data may include raw radio frequency data. According to a further aspect, the image data is extracted from the ultrasound system at various points of the processing pipeline, for instance before the speckle noise filtering step.

According to a further aspect, the image data may include Doppler data which contains velocity information. The Doppler data may be obtained by an additional Doppler-capable ultrasound sensor.

According to a further aspect, the image data may include metadata indicating ultrasound settings, for examples presets such as gain, frequency, and/or dynamic range.

Next, aspects relating to the use of further (non-ultrasound) sensor data are described.

According to an aspect, an additional sensor may be provided (e.g., fixed to the ultrasound probe), and the method may include inputting sensor data from the additional sensor to the machine learning module. The above description of the image data may optionally also apply to the sensor data to the machine learning module.

For example, the additional sensor may comprise an acceleration sensor, the method comprises detecting an acceleration of the ultrasound probe by an acceleration sensor attached to the ultrasound probe; and inputting the acceleration corresponding to the at least two ultrasound image frames into the machine learning module. The acceleration data may be pre-processed, for example, for detecting abrupt motion which the machine learning module may be less able to handle, and for generating an abrupt-motion signal in case of detected abrupt motion.

Instead of or in addition to the data from an acceleration sensor, also any other sensor data may be used, in particular sensor data obtained from an IMU sensor such as acceleration, gyroscopic, magnetic field, barometric data, especially acceleration and/or gyroscopic.

According to a further aspect, the additional sensor may comprise a rotation sensor for detecting a rotation of the ultrasound probe.

According to a further aspect, the method may comprise tracking a position of the ultrasound probe (by a tracking system such as an optical tracking system, e.g., an inside-out tracker being stationary and tracking a marker set attached to the probe, or an outside-in tracker being attached to the probe and tracking a fixed marker set). The probe motion indicator may then be compared and/or combined with the tracking data to identify and/or compensate errors.

Another mode of operation is to detect whether the tracking system fails (e.g., if the tracking marks are obstructed), and if the tracking system is determined to fail, using the determined probe motion indicator as a backup, by substituting the tracked position information from the tracking system by the probe position and orientation determined from the three-dimensional motion indicator (60). Thereby, the method according to this aspect may be used for making an existing tracking system more robust or precise.

According to a further aspect, the additional sensor comprises an optical device (for instance camera, or laser-based motion detecting system).

According to a further aspect, the method comprises generating, as a result of the comparison between the tracking data and the probe motion indicator, a reliability indicator of the probe motion indicator. For example, the method may comprise detecting an inconsistency between the determined three-dimensional motion and the sensor data, and in case of a detected inconsistency, generating an indication that the output is not reliable.

According to a further alternative aspect, no external tracker is provided.

Next, aspects relating to the ultrasound probe are described. According to an aspect, the ultrasound probe comprises an ultrasound transducer array for transmitting ultrasound beams and detecting ultrasound echoes reflected from an object volume of the volume portion at a multiplicity of sample volumes in a scan plane. According to a further aspect, the ultrasound image data is derived from ultrasound echoes reflected from each one of a multiplicity of scan planes through said body portion.

Next, aspects relating to the training data and the acquisition protocol are described.

According to an aspect, the machine learning module has been trained using a training image data stream being obtained using a pre-determined acquisition direction, and the method includes receiving the stream of ultrasound image data from the ultrasound probe while the ultrasound probe is moved along the body portion according to the pre-determined acquisition direction. Optionally, sensor data, synchronized.

According to a further aspect, the training data has been generated by using a separate tracking system which outputs the tracked position and/or motion of the probe for each image frame, and inputting an indicator of the tracked position and/or motion of the probe as a ground truth along with the training image data. Thus, according to an aspect, the training data includes (1) the ultrasound image data, (2) the tracking data as ground truth, and (3) optionally, the sensor data.

The training of the machine learning module can be implemented according to any know machine learning system. The machine learning module typically comprises a model function depending on model parameters (e.g., a neural network), wherein the input of the model function is the image data and other optional input of the machine learning module, and an output is the motion data as a function of the input and the parameters. Typically, the machine learning module is trained by solving an optimization problem for the model function using training data, i.e., input to the model function with known "true" output (ground truth, e.g., the known motion data coming from the accurate tracking system). The optimization problem consists in finding a set f model parameters minimizing a cost function, defined as an error measure between the output of the model function and the ground truth. One example of such an error measure is the squared L2 norm, i.e., the averaged squared difference between the 3 translation and 3 rotation parameters predicted by the model function of the machine learning module, and the ones computed from the tracking data.

Next, aspects relating to the further processing of the probe motion indicator are described. According to an aspect, the method comprises determining, from the probe motion indicator (from the relative three-dimensional displacement and rotation between the ultrasound image frames), a probe position and orientation of the ultrasound probe. The probe position and orientation may be obtained by discrete integration of multiple probe motion indicators.

According to a further aspect, the method comprises filtering of the determined probe position and orientation. For example, the method may comprise further refining and regularizing the probe motion indicator or the determined position and orientation of the probe, e.g., by comparing and/or averaging multiple estimates obtained by the machine learning module.

According to a further aspect, the method may comprise reconstructing a three-dimensional ultrasound image using the determined probe position and orientation and the stream of ultrasound image data, e.g., by any known 3D ultrasound volume compounding and/or reconstruction algorithm, see [Nicholas Rohling, Robert. (1999). 3D Freehand Ultrasound: Reconstruction and Spatial Compounding].

Next, some further aspects are described. According to an aspect, the volume portion is a body portion of a patient. For example, the body portion may include a limb portion such as a forearm portion and/or a leg portion of the patient, for example, for the clinical application of peripheral vein mapping for bypass surgery or AV-fistula mapping.

Alternatively, the volume portion may also be a portion of an article to be inspected non-destructively.

According to a further aspect, the method comprises directly predicting the ultrasound probe motion from the stream of ultrasound images, without the input of any external tracking system, and optionally based on only the image data, i.e., without the input of any sensor data other than the image data.

According to a further aspect, the method is carried out during (i.e., in the context of) acquisition of an ultrasound image of a volume portion by the ultrasound probe. This includes evaluation of previously acquired and stored image data. Preferably, the method (and in particular the determining step) is carried out while the ultrasound data is being acquired, in an at least partially overlapping manner.

According to a further aspect, and apparatus for determining a three-dimensional motion of a movable ultrasound probe 10 during acquisition of an ultrasound image of a volume portion by the ultrasound probe is provided. The apparatus comprises a probe input interface for receiving a stream of ultrasound image data 20 from the ultrasound probe 10 while the ultrasound probe is moved along the volume portion; and a machine-learning module 50. The machine-learning module 50 has an input section adapted for receiving, as an input, at least a sub-set of the ultrasound image data 20, 40 representing a plurality of ultrasound image frames 22, and a training memory section containing a training memory having been trained to determine the relative three-dimensional motion between ultrasound image frames. These parts can be provided by software or by hardware or by a combination of software and hardware. The machine-learning module 50 is adapted for determining, from the input and using the training memory, a three-dimensional motion indicator indicating the relative three-dimensional motion between the ultrasound image frames.

According to a further aspect, the apparatus described herein and in particular the machine-learning module 50 are adapted for carrying out the methods according to any of the embodiments and aspects described herein. Thus, the apparatus may have apparatus parts (modules) for performing each method step described herein. These method steps may be performed by way of hardware components, a computer programmed by appropriate software, by any combination of the two or in any other manner. Thus, in particular, the apparatus comprises a probe input interface for receiving a stream of ultrasound image data 20 from the ultrasound probe 10 while the ultrasound probe is moved along the volume portion. The apparatus further comprises a machine-learning module 50 having an input section adapted for receiving, as an input, at least a sub-set of the ultrasound image data 20, 40 representing a plurality of ultrasound image frames 22, a training memory section containing a training memory having been trained to determine the relative three-dimensional motion between ultrasound image frames. Thereby, the machine-learning module 50 is adapted for determining, from the input and using the training memory, a three-dimensional motion indicator indicating the relative three-dimensional motion between the ultrasound image frames.

According to a further aspect, the motion indicator 60 may be incompletely determined by the machine-learning module 50. In particular, in case the machine-learning module is a convolutional neural network it might be difficult to identify a forward-backward directedness for the motion indicator directly from the output of the machine-learning module (because of the underlying forward-backward symmetry of the problem, as described above). For example, the motion indicator may be a vector or a trajectory describing motion from one image frame A to another image frame B. In general, the motion indicator determined by a convolutional neural network indicates the direction of the motion up to a sign, wherein the sign is related to the forward-backward directedness of the motion. For example, the motion indicator might lack information as to whether image frame A is to the left or to the right of image frame B, or in other words, whether the motion between image frame A and image frame B is a forward or a backward motion.

Next, general aspects relating to the method of determining a three-dimensional directedness-determined motion, including a forward-backward directedness, are described.

According to an aspect, the forward-backward directedness indicates one of two options of a motion, which can go forward or backward with respect to the ultrasound probe. The motion includes a direction which usually on the one hand is given by a path, curve, or the axis of a vector and on the other hand by the forward-backward directedness. The forward-backward directedness indicates whether the motion is in the direction determined for example by a given vector or trajectory or in the exact opposite direction. In other words, the forward-backward directedness is related to a symmetry operation transforming between a forward motion and a backward motion. The forward-backward directedness indicates a sign of the directedness, wherein, for example, a sign change of a vector corresponds to the reversal of the forward-backward directedness. For example, depending on reference (system), the forward-backward directedness is understood to indicate whether a motion goes forward or backward, from left to right or from right to left, from up to down or from down to up, clockwise or counter-clockwise.

According to an aspect, the directedness-indicative data is a data item separate from the motion indicator. The directedness-indicative data may for example, contain a binary information indicating the forward-backward directedness in binary format. According to an aspect, the directedness-indicative data is obtained from a different source, e.g., a different data source such as a different sensor and/or algorithm, than the motion indicator.

According to an aspect, the directedness-indicative data being indicative of the forward-backward directedness of the motion is obtained from a separate data source than the acquired ultrasound images, e.g., from a separate sensor such as an optical sensor. According to an aspect, the directedness-indicative data being indicative of the forward-backward directedness of the motion is obtained from an optical sensor, in particular an optical sensor attacked to the ultrasound probe and/or an optical sensor indicating a movement relative to a surface such as a skin surface. The optical sensor may for example be a laser sensor (similar to the laser sensor used in a mouse), or a camera sensor with a processing unit configured to identify two-dimensional motion of the camera sensor relative to a surface and to extract a forward-backward component from the two-dimensional motion.

According to one aspect, the three-dimensional directedness-determined motion is a motion with explicitly determined forward-backward-directedness. This is in contrast to the three-dimensional motion being an ambiguously determined motion, where the forward-backward-directedness is not explicitly determined. Although the three-dimensional motion includes a forward-backward directedness, it is a default or arbitrary one.

According to one aspect, the three-dimensional directedness-determined motion is described with a directedness-determined motion indicator 96. The directedness-determined motion indicator 96 may be a vector or a trajectory between two image frames. In particular, aspects relating to the motion indicator 60 may also relate to the directedness-determined motion indicator 96 (except aspects relating to forward-backward directedness). It is emphasized that the determination of the directedness-determined motion indicator 96 does not necessarily require a new data value, such as a directedness-determined vector, to be determined, but can also include a calculation rule, for example. Hence, the determination of the directedness-determined motion indicator 96 indicates a functionality resulting from the directedness indicator 66. For example, the directedness indicator can have either the information "+1" or "−1" depending on the forward-backward directedness of motion. If the motion indicator 60 includes a directedness-ambiguously determined vector that in principle describes the motion between image frames at positions A and B, but lacks the forward-backward directedness information, the directedness indicator can be used to determine whether the motion indicator is added to position A ("+1") or subtracted from position A ("−1") in order to arrive at position B. In this way, the relative position of the image frames can be determined without calculating a directedness-determined vector.

According to one aspect, the three-dimensional directedness-determined motion indicator is determined by using the method for determining the motion indicator 60 and some additional steps, comprising receiving directedness-indicative data, inputting at least a subset of the directedness-indicative data into a directedness determining system and determining a directedness indicator. Preferably, the directedness indicator is a binary variable with a first and a second value, e.g. "+1" and "−1", wherein the first value indicates a forward motion and the second value indicates a backward motion.

According to an aspect of the present invention, the forward-backward directedness is obtained outside of the machine learning module 50 and combined with the result of the machine learning module 50 only at a later stage. In this regard, the forward-backward directedness is determined and processed in a fundamentally different manner than other external sensor data fed into the machine learning module. This separated processing takes into account the insight that the problem of determining of the (forward-backward undetermined) motion from a small number of consecutive ultrasound image frames is to a good approximation independent of (and therefore blind to) a change of forward-backward directedness. Therefore, it is advantageous to solve the problem of determining the forward-backward directedness independently of the former problem. Determining the forward-backward directedness of a motion independently may be advantageous as the machine-learning module may be lean and more effective. Moreover, the directedness-determining systems determining the forward-backward directedness of the motion which are disclosed herein are relatively fast and allow (except the implementation using a second machine-learning module) determination of the three-dimensional directedness-determined motion on-the-fly, i.e. extemporaneously while the ultrasound probe is moved along the volume portion.

For the on-the-fly implementations the directedness indicator 66 and the directedness-determined motion indicator 96 may be repetitiously determined for consecutive pairs of ultrasound images, respectively, while the ultrasound probe is moved along the volume portion.

According to one aspect, the steps of receiving a stream of ultrasound image data, inputting at least a sub-set of the ultrasound image data and determining a motion indicator defines a first submethod and the steps of receiving directedness-indicative data, inputting at least a sub-set of the directedness-indicative data and determining a directedness indicator defines a second submethod. The first submethod and the second submethod may run parallel to each other and substantially decoupled from each other. The methods do not have to be fully decoupled as the directedness-indicative data can be received by the ultrasound probe, i.e. the same sensor receiving the image data.

Next, aspects relating to the receiving of directedness-indicative data are described.

According to one aspect, the directedness-indicative data can be received from a tracing system 16 being one of the following or a combination thereof: the ultrasound probe 10, an external sensor 14, 18, wherein, optionally, the latter can be combined with data received from the machine-learning module 50. For example, an accelerometer is in principle able to determine the forward-backward directedness of a motion if it has sufficient accuracy and a filtering method such as the Kalman Filter is used to integrate the acceleration to obtain velocity. However, the combination with the machine learning module is still valid and may also be used in the Kalman Filter to improve the velocity (and therefore forward-backward) estimates.

According to a further aspect, the directedness-indicative data 26 is received as a stream of data, at least partially synchronized with the stream of ultrasound image data 20. At least partially synchronized means that at least a sub-set of the directedness-indicative data is synchronized with at least a sub-set of the ultrasound image data, the sub-sets being spread in time throughout the majority portion of the respective data; Ideally, all of the received data is accompanied with a time stamp such that the individual signals of the ultrasound image data and the directedness-indicative data can be synchronized. Also the data of another external sensor can comprise time stamps in order to synchronize the data streams.

According to a further aspect, the method to determine the forward-backward directedness of the motion comprises usage of the ultrasound probe itself. In one embodiment the forward-backward directedness of the motion can be determined with ultrasound probe with a multi-row ultrasound array comprising an array with a plurality of transducer rows, wherein signals from individual transducer rows are used from the raw IQ data. In another embodiment at least a sub-set of the ultrasound image data received by the ultrasound probe 10 is used as an input for a second machine-learning module 58. The second machine-learning module 58 may be trained to determine a forward-backward directedness of a motion.

Next, aspects relating to the receiving of directedness-indicative data with an external sensor are described.

According to one aspect, the directedness-indicative data can be received from an external sensor 14 or 18. The external sensor may detect position which also includes an angular position of the ultrasound probe. The external sensor may also detect an angular velocity and/or translational velocity of the ultrasound probe. According to one aspect, the external sensor may detect an acceleration of a rotational or translational motion of the ultrasound probe. The external sensor may also detect a displacement of the ultrasound probe 10, in particular, between the ultrasound image frames.

According to one aspect, the directedness-indicative data is received from an external sensor being one of the following or a combination thereof: optical camera, odometer, rotary encoder, position sensor, optoelectronic sensor, accelerometer. According to one aspect, the directedness-indicative data is received from an external sensor used in combination with a rotating element like a sphere or wheel. The external sensor may convert an angular position or motion of a rotating element to a digital output signal. Such external sensor may be a position sensor, a rotary encoder or an odometer. According to one aspect, the rotating element is driven into rotation due to the contact to the underlying surface delimiting the scanned volume portion. According to one aspect, the rotating element slides on the underlying surface.

According to one aspect, the directedness-indicative data is received from an external sensor detecting an acceleration. Such a sensor may be an accelerometer. According to one aspect the accelerometer may be combined with a gyroscope. According to one aspect the accelerometer is used to determine a velocity from acceleration. A Kalman Filter may be used to determine the velocity from acceleration. As a Kalman Filter is a general framework, one could also apply the output from the machine learning module with its estimate of velocity to the filter to determine the forward-backward motion. One option to determine a motion from a fusion of image data and an IMU data using a machine learning model is described in https://arxiv.org/pdf/1803.05850.pdf.

Next, aspects relating to the directedness-determining system are described.

According to a further aspect, the directedness-determining system 56 is not the machine-learning module 50. In general, the directedness-determining system 56 is one of the following or a combination thereof: a second machine-learning module 58, an algorithm calculating the correlation between two data sets of the directedness-indicative data 26 and/or an algorithm converting the directedness-indicative data to a binary variable. Calculating the correlation between two data sets may allow to determine forward-backward directedness of a motion. The correlation is a measure of the relationship or similarity of two data sets which for instance are received at different positions or times. The correlation can be an approach to estimate the relative displacement between two data sets such as images. Calculating a correlation may comprise the concept of using cross-correlation to measure shifts in data sets. Usually, the cross-correlation results in a 1- or 2-dimensional signal whose axes correspond to the displacements in the corresponding directions. By finding the position of the maximum in this image, the most probable displacement can be determined. The forward-backward directedness, e.g. the "+1" or "−1" information, would then be given by the position of the maximum of the cross-correlation (whether left or right from the centre in the corresponding direction). In practical applications, a correlation array is usually computed using Fourier-transform methods as those are much faster than methods directly computing the correlation.

According to one aspect, the directedness-determining system 56 is a second machine-learning module 58 trained to determine a forward-backward directedness of a motion. For this implementation the directedness-indicative data may be the ultrasound image data already inputted in the first machine learning module 50. According to one aspect, the directedness-indicative data comprises a global sequence of the ultrasound image data having a number of ultrasound image frames permitting the identification of characteristic features, particularly anatomical features, of the volume portion. The global sequence of the ultrasound image data may extend over a length of the volume portion extending over at least two relevant anatomical landmarks, e.g. blood vessels, bones, joints or organs. This could be a very small length about 2 cm, e.g. for the belly with many recognizable organs, or a larger length over 5 cm, e.g. in an arm or a leg. According to one aspect, the training for the second machine-learning module uses sequences of ultrasound images acquired on human bodies, such that specific anatomical landmarks accompanied with the human anatomy indicate a forward or backward directedness.

It will be appreciated that elements or features shown with any method, submethod or embodiment herein are exemplary for the specific method or embodiment and may be used on or in combination with other methods, submethods or embodiments disclosed herein. In particular, further disclosed herein is the subject-matter of the following clauses:

1. Method of determining a three-dimensional motion of a movable ultrasound probe (10) during acquisition of an ultrasound image of a volume portion (2) by the ultrasound probe, the method comprising:
   Receiving a stream of ultrasound image data (20) from the ultrasound probe (10) while the ultrasound probe is moved along the volume portion (2);
   Obtaining motion-indicative input data representing at least a direction of movement of the ultrasound probe along the volume portion (2);
   Inputting at least a sub-set of the ultrasound image data (20, 40) representing a plurality of ultrasound image frames (22) into a machine-learning module (50), wherein
   the machine learning module (50) has been trained to determine the relative three-dimensional motion between ultrasound image frames (22);
   Inputting sensor data into the machine-learning module (50), wherein the sensor data describes a translational motion of the ultrasound probe with respect to the orientation of the ultrasound probe relative to the volume portion (2) [while the ultrasound probe is moved along the volume portion (2)]; and
   Determining, by the machine-learning module (50), a three-dimensional motion indicator (60) indicating the relative three-dimensional motion between the ultrasound image frames.

2. Method according to clause 1, further comprising pre-processing the ultrasound image data, the pre-processing including at least one of an image filtering, image resampling and image segmentation.

3. Method according to any one of the preceding clauses, wherein the machine learning module (50) comprises a neural network, preferably a convolutional neural network.

4. Method according to any one of the preceding clauses, wherein
the step of inputting the at least sub-set of the ultrasound image data (20, 40) includes inputting local image data corresponding to a pair of ultrasound image frames (22) to the machine learning module (50), and wherein
the three-dimensional motion indicator (60) indicates the relative three-dimensional motion between the pair of ultrasound image frames (22), and wherein
the inputting and determining steps are repeated for consecutive pairs or subsets of image frames.

5. Method according to any one of the preceding clauses, wherein
the step of inputting the at least sub-set of the ultrasound image data (20, 40) includes inputting a global set of image data substantially spanning the whole set of ultrasound image frames (22) to the machine learning module (50), and wherein
the three-dimensional motion indicator (60) indicates the relative three-dimensional motion for determining the relative three-dimensional motion of each of the ultrasound image frames (22) with respect to a first one of the ultrasound image frames.

6. Method according to any one of the preceding clauses, wherein the ultrasound image data (20, 40) includes at least one of A-Mode data, B-Mode data, continuous harmonic imaging data, Doppler data, plain wave imaging data, and raw radio frequency data.

7. Method according to any one of the preceding clauses, further comprising inputting further sensor data into a machine-learning module (50), wherein the further sensor data is synchronized with the ultrasound image data (20, 40).

8. Method according to the preceding clause, wherein the further sensor data includes at least one of position data, e.g., obtained by a tracking system, acceleration data representing the acceleration corresponding to the at least two ultrasound image frames, gyroscope data, magnetic measurement data, and barometer data.

9. Method according to any one of the preceding two clauses, further comprising detecting an inconsistency between the determined three-dimensional motion indicator (60) and the sensor data.

10. Method according to any one of the preceding clauses, further comprising determining, from the three-dimensional motion indicator (60), a probe position and orientation of the ultrasound probe (10) for each image frame (22).

11. Method according to the preceding clause, further comprising tracking the position of the movable ultrasound probe (10) by a further tracking system thereby generating a tracked position information, detecting whether the tracking system fails, and if the tracking system is determined to fail, substituting the tracked position information by the probe position and orientation determined from the three-dimensional motion indicator (60).

12. Method according to any one of the preceding two clauses, further comprising reconstructing a three-dimensional ultrasound image using the stream of ultrasound image data and the probe position and orientation determined from the three-dimensional motion indicator (60).

13. Method according to any one of the preceding clauses, wherein the method comprises directly predicting the ultrasound probe motion from the stream of ultrasound images using the three-dimensional motion indicator (60), without using a further tracking system.

14. Apparatus for determining a three-dimensional motion of a movable ultrasound probe (10) during acquisition of an ultrasound image of a volume portion by the ultrasound probe, the apparatus comprising:
   a probe input interface for receiving a stream of ultrasound image data (20) from the ultrasound probe (10) while the ultrasound probe is moved along the volume portion; and a machine-learning module (50) having
  (a) an input section adapted for receiving, as an input, at least a sub-set of the ultrasound image data (20, 40) representing a plurality of ultrasound image frames (22),
  (b) a training memory section containing a training memory having been trained to determine the relative three-dimensional motion between ultrasound image frames, wherein
the machine-learning module (50) is adapted for determining, from the input and using the training memory, a three-dimensional motion indicator indicating the relative three-dimensional motion between the ultrasound image frames.

REFERENCE SIGNS 2 volume portion/body portion
10 ultrasound probe
11 ultrasound system
12 motion of ultrasound probe
14 Sensor
16 Tracing system
20 ultrasound image data
22 imaging region (image plane) of image frames
24 sensor data
26 directedness-indicative data
30 (image data) pre-processing module
34 (sensor data) pre-processing module
36 (directedness-indicative data) pre-processing module
40 pre-processed ultrasound image data
44 pre-processed sensor data
46 (pre-processed) directedness-indicative data
50 machine learning module
52 training data
56 directedness-determining system
60 motion indicator
66 directedness indicator
70 post-processing module
80 post-processed trajectory data
82 determined spatial arrangement of image frames
86 (directedness-determined motion indicator) determining module
90 camera
91 marker
92 image
93 Optoelectronic sensor
94 low-resolution image
95a,b transducer rows
96 directedness-determined motion indicator
98 (directedness-determined motion indicator) post-processing module
99 (directedness-determined motion indicator) post-processed trajectory data
$I_1, I_2, \ldots I_N$ image frames
$C_1, C_2, \ldots C_N$ determined spatial arrangement of image frame coordinate systems
$M_{12}$ coordinate transformation function for image frame coordinate systems

The invention claimed is:

1. A method of determining a three-dimensional directedness-determined motion, including a forward-backward directedness, describing the motion of a movable ultrasound probe during acquisition of an ultrasound image of a volume portion by the ultrasound probe, the method comprising:

Receiving a stream of ultrasound image data from the ultrasound probe while the ultrasound probe is moved along the volume portion;

Inputting at least a subset of the ultrasound image data representing a plurality of ultrasound image frames into a machine-learning module, wherein the machine learning module has been trained to determine a three-dimensional motion between ultrasound image frames;

Determining, by the machine-learning module, a motion indicator indicating a three-dimensional motion between the ultrasound image frames;

Receiving directedness-indicative data being indicative of the forward-backward directedness of the motion, from a separate data source than the acquired ultrasound image data;

Inputting at least a sub-set of the directedness-indicative data into a directedness-determining system; and Determining, by the directedness-determining system, a directedness indicator of the three-dimensional motion between the ultrasound image frames; and Determining a directedness-determined motion indicator indicating the three-dimensional directedness-determined motion, including a determined forward-backward directedness of the motion, between the ultrasound image frames from the motion indicator and the directedness indicator, wherein forward and backward refer to opposite sides of the ultrasound probe along a line perpendicular to the ultrasound image plane.

2. The method according to claim 1, wherein the directedness-indicative data is received as a stream of data, at least partially synchronized with the stream of ultrasound image data.

3. The method according to claim 1, wherein the directedness indicator is a binary variable with a first and a second value, wherein the first value indicates a forward directedness of the motion and the second value indicates a backward directedness of the motion.

4. The method according to claim 1, wherein the steps of receiving a stream of ultrasound image data, inputting at least a sub-set of the ultrasound image data and determining a motion indicator defines a first submethod and the steps of receiving directedness-indicative data, inputting at least a sub-set of the directedness-indicative data and determining a directedness indicator defines a second submethod; and wherein the first submethod and the second submethod run parallel to each other and substantially decoupled from each other.

5. The method according to claim 1, wherein the motion indicator, the directedness indicator and the directedness-determined motion indicator are repetitiously determined for consecutive pairs of ultrasound images, respectively, while the ultrasound probe is moved along the volume portion.

6. The method according to claim 1, wherein the directedness-indicative data is received by the ultrasound probe, and wherein the step of inputting at least a sub-set of the directedness-indicative data into a directedness-determining system comprises inputting the sub-set of the ultrasound image data into a second machine-learning module, wherein the second machine learning module has been trained to determine a forward-backward directedness of a motion.

7. The method according to claim 1, wherein the subset of the directedness-indicative data comprises a global sequence of the ultrasound image data having a number of ultrasound image frames permitting the identification of anatomical features of the volume portion.

8. The method according to claim 1, wherein the ultrasound probe includes a multi-row ultrasound array and wherein the directedness-indicative data is received from raw ultrasound data received from individual rows of the array.

9. The method according to claim 1, wherein the directedness-indicative data is received from an external sensor while the ultrasound probe is moved along the volume portion; wherein the external sensor detects position, velocity, acceleration and/or displacement of the ultrasound probe.

10. The method according to claim 1, wherein the directedness-indicative data is received from an external tracking system tracking a position of the ultrasound probe.

11. The method according to claim 10, wherein the external tracking system is an optical tracking system.

12. The method according to claim 11, wherein the external tracking system is-an optical camera, used in combination with a marker set.

13. The method according to claim 12, wherein the optical tracking system is stationary and tracks a marker set fixed to the ultrasound probe or wherein the optical tracking system is attached to the ultrasound probe and tracks marker sets in an environment.

14. The method according to claim 1, wherein the directedness-indicative data is received from at least one of the following:
- an external sensor attached to the ultrasound probe, wherein the external sensor is adapted to detect a one- or two-dimensional motion, relative to an underlying surface delimiting the volume portion;
- an optoelectronic sensor used in combination with a light emitter, wherein the optoelectronic sensor receives pattern images from an underlying surface delimiting the volume portion;
- an external sensor detecting the angular motion of a rotating element; wherein the rotating element is driven in rotation due to the motion of the ultrasound probe on an underlying surface delimiting the volume portion.

15. The method according to claim 1, wherein the directedness-indicative data is acceleration data received by an accelerometer, wherein the acceleration data represents the acceleration corresponding to the at least two ultrasound image frames, and wherein the step of determining the directedness indicator comprises integration of the acceleration data.

16. The method according to claim 1, further comprising inputting further sensor data into the machine-learning module, wherein the further sensor data is synchronized with the ultrasound image data and, wherein the machine learning module comprises a convolutional neural network, and wherein the sensor data is inputted after a plurality of convolutional and max pooling layers, and before final output layers and/or final fully connected layers.

17. Method according to claim 1, wherein the directedness-indicative data is received from an optical tracking system.

18. An apparatus for determining a three-dimensional motion, including a forward-backward directedness of the motion, of a movable ultrasound probe during acquisition of an ultrasound image of a volume portion by the ultrasound probe, the apparatus comprising:
- a probe input interface for receiving a stream of ultrasound image data from the ultrasound probe while the ultrasound probe is moved along the volume portion;
- a tracing system configured to receive directedness-indicative data being indicative of the forward-backward directedness of the motion, from a separate data source than the acquired ultrasound image data;
- a machine-learning module having (a) an input section adapted for receiving, as an input, at least a sub-set of the ultrasound image data representing a plurality of ultrasound image frames, (b) a training memory section containing a training memory having been trained to determine the relative three-dimensional motion between ultrasound image frames, wherein the machine-learning module is adapted for determining, from the input and using the training memory, a three-dimensional motion indicator indicating the relative three-dimensional motion between the ultrasound image frames;

- a directedness-determining system configured to determine a directedness indicator of the three-dimensional motion between the ultrasound image frames by using at least a sub-set of the directedness-indicative data;
- a motion-determining system configured to determine a directedness-determined motion indicator indicating the three-dimensional motion between the ultrasound image frames by using the motion indicator and the directedness indicator of the three-dimensional motion between the ultrasound image frames, wherein forward and backward refer to opposite sides of the ultrasound probe along a line perpendicular to the ultrasound image plane.

* * * * *